(12) United States Patent
Freiderikos et al.

(10) Patent No.: US 11,548,221 B2
(45) Date of Patent: Jan. 10, 2023

(54) SYSTEM AND METHOD FOR PRODUCING PHARMACUTICAL OBJECTS VIA 3D PRINTING

(71) Applicant: PHARMAPRINT LIMITED LLC, Wollerau (CH)

(72) Inventors: Achillefs Freiderikos, Kalithea Athens (GR); Konstantinos Theodosopoulos, Exarchia Athens (GR); Arne-Patrik Heinze, Hamburg (DE)

(73) Assignee: PHARMAPRINT LIMITED LLC, Wollerau (CH)

( * ) Notice: Subject to any disclaimer, the term of this patent is extended or adjusted under 35 U.S.C. 154(b) by 280 days.

(21) Appl. No.: 16/611,389

(22) PCT Filed: May 7, 2018

(86) PCT No.: PCT/EP2018/061707
§ 371 (c)(1),
(2) Date: Nov. 6, 2019

(87) PCT Pub. No.: WO2018/206497
PCT Pub. Date: Nov. 15, 2018

(65) Prior Publication Data
US 2020/0188307 A1 Jun. 18, 2020

(30) Foreign Application Priority Data
May 11, 2017 (GR) .............................. 20170100219

(51) Int. Cl.
*B29C 64/209* (2017.01)
*B33Y 10/00* (2015.01)
(Continued)

(52) U.S. Cl.
CPC .......... *B29C 64/209* (2017.08); *A61K 9/2095* (2013.01); *A61K 45/06* (2013.01);
(Continued)

(58) Field of Classification Search
CPC ....... A61J 3/02; A61J 3/06; A61J 3/07; A61K 45/06; A61K 9/2095; B29C 64/118;
(Continued)

(56) References Cited

U.S. PATENT DOCUMENTS 5,121,329 A * 6/1992 Crump .................... B29C 64/40
228/180.5
5,303,141 A * 4/1994 Batchelder ............. B33Y 70/00
156/244.11
(Continued)

FOREIGN PATENT DOCUMENTS

CN          1450953       10/2003
CN        103 878 980 A    6/2014
(Continued)

OTHER PUBLICATIONS

Chinese Office Action Corresponding to 2018800403738 dated Apr. 25, 2021.
(Continued)

*Primary Examiner* — Manley L Cummins, IV
(74) *Attorney, Agent, or Firm* — Finch & Maloney PLLC

(57) ABSTRACT

A system for producing pharmaceutical objects, such as tablets, granules and capsules, via 3D printing. The system comprises a 3D printing machine (2) with a mechanical system (3) movable in one or more directions, at least one print head (5) with a nozzle (37) being movable by the mechanical system and a base system (4) carrying a print base (6) for receiving a prepared mixture (27) applied by the print head (5). The system comprises at least one carrier (35) for holding a cartridge (28). Printing is done at formatted print locations (49) on the base (6). A method for producing pharmaceutical objects by providing at least one pharmaceutical substance in at least one cartridge, placing the cartridge in a carrier, establishing a fluid connection between a cartridge and a print head, moving the print head nozzle (Continued)

according to a program and dispensing the pharmaceutical substance to a print base.

19 Claims, 24 Drawing Sheets

(51) Int. Cl.
| | |
|---|---|
| *B33Y 30/00* | (2015.01) |
| *B29C 64/112* | (2017.01) |
| *B29C 64/118* | (2017.01) |
| *B29C 64/165* | (2017.01) |
| *B29C 64/336* | (2017.01) |
| *A61K 9/20* | (2006.01) |
| *A61K 45/06* | (2006.01) |
| *B29C 64/245* | (2017.01) |
| *B29C 64/364* | (2017.01) |
| *B29C 64/35* | (2017.01) |
| *B29C 64/106* | (2017.01) |

(52) U.S. Cl.
CPC .......... *B29C 64/106* (2017.08); *B29C 64/112* (2017.08); *B29C 64/118* (2017.08); *B29C 64/165* (2017.08); *B29C 64/245* (2017.08); *B29C 64/336* (2017.08); *B29C 64/35* (2017.08); *B29C 64/364* (2017.08); *B33Y 10/00* (2014.12); *B33Y 30/00* (2014.12)

(58) Field of Classification Search
CPC ... B29C 64/165; B29C 64/209; B29C 64/336; B29C 64/35; B29C 64/364
See application file for complete search history.

(56) References Cited

U.S. PATENT DOCUMENTS

| | | | | |
|---|---|---|---|---|
| 5,764,521 | A * | 6/1998 | Batchelder | B29C 48/92 425/149 |
| 7,891,964 | B2 * | 2/2011 | Skubic | B29C 48/37 425/375 |
| 10,670,019 | B2 * | 6/2020 | Zinniel | B29C 64/118 |
| 2002/0015728 | A1 | 2/2002 | Payumo et al. | |
| 2003/0063138 | A1 | 4/2003 | Varnon et al. | |
| 2003/0090034 | A1 | 5/2003 | Mulhaupt et al. | |
| 2004/0003738 | A1 * | 1/2004 | Imiolek | B33Y 30/00 101/480 |
| 2004/0170459 | A1 | 9/2004 | Taylor et al. | |
| 2006/0127153 | A1 * | 6/2006 | Menchik | B29C 64/112 400/62 |
| 2006/0156978 | A1 * | 7/2006 | Lipson | B33Y 30/00 438/3 |
| 2010/0327479 | A1 * | 12/2010 | Zinniel | B29C 64/106 425/114 |
| 2011/0172611 | A1 | 7/2011 | Yoo et al. | |
| 2012/0074614 | A1 | 3/2012 | Sowden et al. | |
| 2013/0073068 | A1 | 3/2013 | Napadensky | |
| 2013/0333798 | A1 | 12/2013 | Bosveld et al. | |
| 2015/0037445 | A1 | 2/2015 | Murphy et al. | |
| 2015/0084238 | A1 | 3/2015 | Bonassar et al. | |
| 2015/0105891 | A1 * | 4/2015 | Golway | C12M 33/00 700/98 |
| 2015/0137402 | A1 * | 5/2015 | Schmehl | B29C 48/02 264/39 |
| 2015/0197063 | A1 | 7/2015 | Shinar et al. | |
| 2015/0217514 | A1 * | 8/2015 | Maier | B29C 64/255 264/241 |
| 2016/0046832 | A1 | 2/2016 | Wroblesky et al. | |
| 2016/0121546 | A1 | 5/2016 | Yao et al. | |
| 2016/0122541 | A1 | 5/2016 | Jaker et al. | |
| 2016/0200024 | A1 * | 7/2016 | Kim | B29C 48/832 425/375 |
| 2017/0066083 | A1 | 3/2017 | Shioya et al. | |
| 2018/0079033 | A1 | 3/2018 | Krueger et al. | |
| 2018/0141275 | A1 * | 5/2018 | Patel | B33Y 10/00 |
| 2018/0169947 | A1 * | 6/2018 | Jessen | B29C 64/268 |
| 2019/0125681 | A1 * | 5/2019 | Albed Alhnan | B29C 64/314 |

FOREIGN PATENT DOCUMENTS

| | | |
|---|---|---|
| CN | 104224405 | 12/2014 |
| CN | 104826762 | 8/2015 |
| CN | 105922593 | 9/2016 |
| CN | 106513673 | 3/2017 |
| JP | 2010-100883 A | 5/2010 |
| WO | 2004005014 A2 | 1/2004 |
| WO | 2004/044816 A1 | 5/2004 |
| WO | 2006/020685 A2 | 2/2006 |
| WO | 2014/144630 A1 | 9/2014 |
| WO | 2015/054577 A1 | 4/2015 |
| WO | 2016/038356 | 3/2016 |
| WO | 2016/150721 A1 | 9/2016 |
| WO | 2016/184997 A1 | 11/2016 |
| WO | 2017/034951 A1 | 3/2017 |

OTHER PUBLICATIONS

European Office Action Corresponding to 18723797.9 dated May 19, 2020.
Russian Office Action Corresponding to 2019140450 dated Jul. 1, 2021.
Indian Office Action Corresponding to 201917044765 dated Jan. 19, 2022.
International Search Report Corresponding to PCT/EP2018/061707 dated Nov. 8, 2018.
Written Opinion Corresponding to PCT/EP2018/061707 dated Nov. 8, 2018.

* cited by examiner (a)  (b)

(a) (b) (c)

SYSTEM AND METHOD FOR PRODUCING PHARMACUTICAL OBJECTS VIA 3D PRINTING

The invention relates to a system and a method for producing pharmaceutical objects via 3D printing.

The invention in particular relates to the art of manufacturing 3D objects by applying, accumulating or creating layers for the creation of 3D printed articles and in particular to a system which is specially modified for the manufacture of multiple tablets, granules, capsules, suppositories, implants and other pharmaceutical items.

The system disclosed in this invention for producing tablets, granules and capsules by means of 3D printing has not been disclosed in the prior art. Until now, 3D printing has in no way been widely applied in the field of pharmaceutics and production of pharmaceutical or non-pharmaceutical tablets, granules or capsules.

Only the WO2017034951 is known in the state of the art, which discloses a 3D printing device and system for the production of pharmaceutical tablets. According to that invention, a powdered mixture is applied on a moving belt, creating the first layer of the tablet before spraying a binding fluid which unifies the mixture and prepares it to receive the next layer. This process is repeated many times resulting in the creation of a solid but particularly porous tablet which is orally dispersible by water.

A major disadvantage of that particular invention is the method of making the tablets, as it is carried out by constantly applying a mixture, a part of which is not used for the preparation of the tablet, resulting in feedstock waste. Furthermore, it is a limiting factor that the device can produce exclusively porous tablets using a powder blend which prevents the manufacture of other types, such as capsules or compact granules, and does not provide for the possibility of printing objects by using a fluid feedstock, the printing process being carried out by continuously applying layers of material in repetitive steps until the formation of the porous tablet.

Most drugs are administered through the digestive tract for the purpose of intestinal absorption, or entry into the blood-stream from the mucosa of the mouth or the mucosa of the rectum. Ingestion of medicaments presents multiple advantages as it is painless and easy, dissolution of the drug is facilitated by abundant digestive secretions, while changes in pH along the digestive tract provide a suitable environment for absorption in virtually all drugs. In addition, great mobility, large surface and abundant blood supply of the digestive mucosa greatly facilitate absorption. The rate of absorption can be varied depending on the tablet formulation, e.g., the ease of disintegration, the solubility of the casing, and/or the size of the granules contained in a capsule. Finally, the relatively slow absorption by the digestive system allows the possibility of early intervention in case of any error.

Although production of drugs administered via the digestive tract shows a number of advantages, production of granules, tablets, capsules and the related pharmaceutical or non-pharmaceutical formulations has been a complex and particularly costly process so far. The costs of research and development of new medicines, the production units, the specialized machinery and materials used to produce medicines, and the increased labour costs contribute to a significant increase in the price of a drug.

A further drawback is due to the high cost of maintaining quantities of medicines for emergencies. Especially in remote and inaccessible areas, the potential emergency leads to the storage of quantities of drugs, which are often left unused until the expiry date.

It is therefore an object of the present invention to advantageously overcome the abovementioned drawbacks and deficits of the prior art by proposing a system of production of pharmaceutical objects, such as tablets, granules and capsules, by means of 3D printing.

A further object of the present invention is to provide the proposed system for producing pharmaceutical objects, such as tablets, granules and capsules, by means of 3D printing, for the production of individual prints at the choice of the individual user.

The problem is solved by a system for producing pharmaceutical objects, such as tablets, granules and capsules, via 3D printing comprising a 3D printing machine with a mechanical system movable in one or more directions.

In the context of this invention pharmaceutical objects shall comprise pills, tablets, granules and capsules, suppositories, implants and other pharmaceutical items, which are administered to or placed in a mammal body.

The system further comprises at least one print head with a nozzle being movable by the mechanical system. The system preferably comprises one print head.

The system further comprises a base system carrying a base for receiving a prepared mixture applied by the print head.

The print head perform the action of printing products of this system, by dispensing repeated layers of substance on top of a print base so to form a predefined shape object.

The print head comprises a least one printing nozzle. The nozzle is the part of the print head to allow the flow of material on the print base. They may have or may not have a valve to control flow of substance depending on the characteristics of various fluid substances, such as powders, granules, liquids, gels, creams, pastes etc.

The system further comprises at least one carrier for holding at least one cartridge, wherein the cartridge contains a printable substance. The cartridge may be removed and/or replaced.

The cartridges may each contain one or more of a variety of active substances (API) including—but not limited to—the families of: antibiotics, statines, stimulants, antiseptics, antipyretics, chemotherapeutics, anti-inflammatories, anti-fungines, hormone medication substances, diuretics, contraceptives, psychotropics (antidepressants, anti-psychotics etc.) etc.

The cartridges may contain one or more of a variety of excipients including—but not limited to—binders, coatings, anti-adherents, colors, flavors, resin, glidants, lubricants, sorbents, vehicles, sweeteners, solvents, inert powders, biodegradable polymers, waxes, preservatives, disintegrants etc.

The cartridges may contain one or more of a variety of substances used in oriental medicine including—but not limited to—herbal pharmacology substances etc.

The cartridges may contain one or more of a variety of substances used in homeopathic medicine including—but not limited to—tinctures etc.h The cartridges may contain one or more of a variety of substances used in bio-engineering medicine including—but not limited to—stem cells etc..

The cartridges may contain one or more of a variety of composite substances created—in any suitable—mixing analogy from any of the aforementioned substance families.

The cartridges may contain a variety of substances that may be still under development or research, and not yet disclosed.

It is a advantage of the present invention to provide a system for producing pharmaceutical objects, such as tablets, capsules and granules, by means of 3D printing, which can use cartridges having the corresponding active substance and the corresponding plastic or cohesive substance to be used in 3D printing.

When a cartridge is empty or when another substance is needed the cartridge may be removed from the carrier and a new cartridge may be inserted.

A further advantage of the invention in order to make the present invention useful is to provide systems for producing pharmaceutical objects, such as tablets, capsules and granules, in different sizes and with optionally additional capabilities, covering the simple yet more complex 3D print requirements.

Furthermore, the system may comprise a plurality of carriers for cartridges each containing a different substance for sequential or simultaneous printing of more than one drug at a time.

The carriers may hold a plurality of cartridges with a specific set of printable substances for printing a certain class of pharmaceutical objects. When a pharmaceutical object of a different class shall be printed, the whole plurality of cartridges may be replaced.

In an advantageous embodiment the system has more than one print head.

The mechanical system may comprise a mechanical arm which ends in a print head and which can be moved in one, two or three directions, accurately printing through the head the article required at a time.

A robotic arm is an example of a mechanical arm, usually programmable, with similar functions to a human arm; the arm may be the sum total of the mechanism or may be part of a more complex robot. The links of such a manipulator are connected by joints allowing either rotational motion (such as in an articulated robot) or translational (linear) displacement. The links of the manipulator can be considered to form a kinematic chain. The terminus of the kinematic chain of the manipulator is called the end effector and it is analogous to the human hand.

For the needs of the present system the following types of robotic arms may be used:
  Cartesian robot/Gantry robot: Used for pick and place work, application of sealant, assembly operations, handling machine tools and arc welding. It's a robot whose arm has three prismatic joints, whose axes are coincident with a Cartesian coordinator.
  Cylindrical robot: Used for assembly operations, handling at machine tools, spot welding, and handling at die-casting machines. It's a robot whose axes form a cylindrical coordinate system.
  Spherical robot/Polar robot Used for handling machine tools, spot welding, die-casting, fettling machines, gas welding and arc welding. It's a robot whose axes form a polar coordinate system.
  SCARA robot: Used for pick and place work, application of sealant, assembly operations and handling machine tools. This robot features two parallel rotary joints to provide compliance in a plane.
  Articulated robot: Used for assembly operations, die-casting, fettling machines, gas welding, arc welding and spray painting. It's a robot whose arm has at least three rotary joints.
  Parallel robot: One use is a mobile platform handling cockpit flight simulators. It's a robot whose arms have concurrent prismatic or rotary joints.
  Anthropomorphic robot: It is shaped in a way that resembles a human hand, as example with independent fingers and thumbs.

The mechanical system may comprise a scaffold, also called bridge, which is the mechanical structure commonly used in 3d printers. The scaffold consists of structures being vertical and parallel to the ground. The scaffold carries the print head and moves it in an up/down direction and/or in x-direction and/or in y-direction or remains still with the print base doing all the movements necessary.

The system may comprise a fed line for establishing a fluid connection between the carrier and the print head. The printing substance may flow through the fed line from a cartridge in the carrier to the print head. The print line may be flexible such that the carrier may stay at a fixed position while the print head is moved to the printing position by the mechanical system.

Alternatively the carrier and the print head may be brought closely to each other to establish a direct fluid connection between a cartridge in a carrier and the print head.

Preferably the system comprises a magazine unit with at least one carrier, preferably a plurality of carriers.

In particular at least a part of the magazine unit is moveable, such that the carrier may perform a motion.

For example by movement of the magazine unit a cartridge being held in one of a plurality of carriers may be transported to a delivery position, where a fluid connection between the cartridge and the print head may be established. After another movement of the magazine unit another cartridge may be moved to the delivery position, such that a plurality of substances may be successively filled in the print head.

The magazine unit may comprise an actuator, in particular a servomotor, a pneumatic drive, a hydraulic drive, a chain drive or a magnetic drive to enable the movement of at least a part of the magazine unit, in particularly to enable the movement of a carriers or of a plurality of carriers.

A plurality of carriers may be arranged on a carousel, such that for moving a single cartridge all carriers have to be moved. A plurality of carriers may alternatively be arranged in line on a guide rail and may be shifted to be brought in a delivery position.

In a preferred embodiment of the system comprises at least one moveable push rod, preferably attached to the carrier, for discharging a cartridge. Hence the cartridges used for the system do not need mechanical equipment for discharging them. A moveable push rod and an actuator for moving the pushrod provide for exact and reproducible dosing an amount of a substance measured according to a selected recipe.

The system may further comprise an opening device, preferably connected with the carrier, for opening a cartridge. For example the carrier may comprise a needle for punching into a cartridge, a cap remover or a pin for opening a valve of the cartridge.

The system may further comprise a closing device, preferably connected with the carrier, for at least temporarily closing a cartridge during a time when it is not needed for printing.

The system may comprise a reading unit, preferably connected with the carrier, for identifying an identification mark on a cartridge. Hence the system may recognize a kind of substance contained in the cartridge, a use-by date, a target quantity or other data associated with the cartridge.

The reading unit allows logistic support like statistics or automated order for refills. Logistics benefit volume and weight reduction as well as energy consumption needs.

In a preferred embodiment of the system the system comprises a carrier with a temperature control device. The carrier may provide for heating and/or cooling the cartridges.

In a preferred embodiment of the system the system comprises a print head with a temperature control device. The print head may be heatable and/or coolable.

In particular the print head comprises a print head body with indentations, fins or channels for guiding a tempering agent, for example a tempering fluid or a tempering gas, like cooling air. Alternatively the print head may comprise a thermal conductor which may be heated electrically.

The print head may be covered by a thermal insulation mantle if high temperature is required.

In a preferred embodiment the print head comprises a print head body providing a volume for a printing substance. The print head body may comprise an opening for receiving a fluid substance from a cartridge, which in particular is connectable to a fed line.

Advantageously the print head comprises a stirring and/or discharge tool, in particular a worm screw, being arranged in the printing head body.

The stirring and/or discharge tool may be moveable for example rotatable within a print head body.

A mixing tool provides for mixing a plurality of substances delivered from a plurality of cartridges into the print head.

A discharge tool may provide for discharging a certain amount of substance through the print head during printing. The discharge tool may be a pushing tool, which is moveable in the print head body. The print head may comprise a tool which is suitable for mixing and pushing.

Preferably the system comprises an actuator for moving the stirring and/or pushing tool.

Alternatively the print head my comprise a discharge tool for reducing the size of the print head body, for example a squeezing tool or a collapsing tool, such that substance is pressed out of the print head nozzle, when the volume of the print head body is reduced.

Preferably the system comprises an actuator for moving the discharge tool.

The print head may comprise a double body: a) an external cylindrical—or other—shape hard body, preferably made from a recyclable material, and b) an inner container made from elastic/flexible/compressible material. On the upper part there could be a plug and on the lower part a cap connected to both bodies and fitted with a printing nozzle possibly fitted with a valve.

It is a further advantage of the invention to provide a system for producing pharmaceutical objects, such as tablets, granules and capsules, by means of 3D printing, which has a pushing tool comprising a punch head to push the proper amount of substance out of the print head at a time in order to print the drug.

In a preferred embodiment the print head comprises a tool which is suitable for mixing and pushing. For this purpose the stirring tool may be at least partly collapsible, in particular the stirring tool comprises a collapsible head.

The stirring tool with the collapsing head may be made of Kevlar, of carbon fibres or of an epoxy raisin.

The collapsing head may provide for a vacuum effect at the print head nozzle to prevent dripping.

Advantageously the print head comprises a nozzle with a valve, for example a check valve, a shutter valve, a ball valve or a pin valve.

The print head my comprise a spray nozzle and a supply line for compressed air, steam, water, solvents, pharmaceutical inks, alimentary colored inks and more.

The steam could offer bonding to very dry substances, allowing very rapid production rates and very porous finished products. The steam may accelerate pharmacokinetics.

The same may be done with a combination of steam and adhesives and pharmaceutical binders/solvents and water.

Pressurized air could help either drying the items under production, or to be used in the same way as the steam but with pills (etc.) created out of substances that could be affected by heat and/or water.

Colored inks could be used to mark different dosages.

In a beneficial embodiment of the invention the system comprises a thermal print head equipped with a worm screw to stir the mixture prior to 3D printing.

Still another advantage of the invention is the presentation of a collapsible print head which, in addition to stirring, also extracts the air from the mixture, creating more compact tablets, granules or capsules when required.

Advantageously the system comprises an energy emitter, which is linked to the print head. The energy emitter may be arranged on mechanical system and may be moved together with the print head or the energy emitter may be directly attached to the print head. The energy emitter provides for drying or fixing an amount of a substance after it has left the print head nozzle.

In particular the energy emitter is a photopolymer headlamp, an IR emitter, a laser, a microwave emitter, a liquid nitrogen spray nozzle, a compressed air nozzle or a steam nozzle.

The print head may comprise a plurality of nozzles. Hence a plurality of pharmaceutical objects may be printed in parallel.

In an expedient embodiment of the invention the system comprises a cleaning unit for cleaning the print head and/or a cartridge. The cleaning unit may comprise a wash tank and/or a wash port. The wash port may be connectable to a cleaning fluid reservoir and/or a cleaning fluid filtration system.

After usage the print head, preferably together with a stirring and/or pushing tool, may be cleaned, such there is no contamination of the print head when used the next time, with a different recipe.

The cleaning unit may be a special place reserved in the 3d printing system. The cleaning unit may comprise an enclosed area with doors that are necessary for the print heads to be brought in.

These doors, or openings, preferably have all the necessary automation so to be controlled-open-close-lock and monitored as well as every other mechanism inside this area.

The doors or openings preferably have the necessary sealing so to render enclosed area isolated from the rest of the system volume in a way not to compromise vital functions of the system, like the vacuum and the climate control—when these are in use—by evaporation of liquids in use and storage here or by the use of steam. The print head, right after their use is moved here be the mechanical system.

The cleaning unit preferably comprises a heated air supply for drying the print head, nozzles for dispensing steam, compressed air, water and/or solvent spray, a vacuum suction to remove steam and excess liquids, brushes, needles for cleaning very narrow nozzles, valves, breather valves, a tank containing solvents and/or water, in which the print head may be immersed and cleaned, an ultrasound emitter and/or a dedicated cleaning laser emitter.

The tank may comprise a liquid circulation system which may comprise circulators, filters, such as active carbon filters, micro-filters, and dedicated pharmaceutical filters like HEPA H13 filters, and their necessary tubing.

In a preferred embodiment of the invention the system comprises a temperature control system for adjusting the temperature of the print base. The print base system may comprise air ducts or channels for guiding a tempering agent, for example a tempering fluid or a tempering gas, like cooling air.

The temperature of the print base may be adjusted in a range from −5° C. to 40° C. Preferably the print base is heated to assist evaporation and to promote drying of the printed objects.

Advantageously the system comprises a print base comprising formatted printing locations for shaping the pharmaceutical object, in particular convex recesses. The substance may be printed on a receptive formatted printing location, which affects the shape of the pharmaceutical object. The bottom side of the object may for example have a convex shape rather than a flat plain.

Formatted printing locations allow for creating a pharmaceutical object, such as a pill, having a form as the majority of such objects, for example pills, made by traditional means have. They may have a symmetrical lenticular shape.

Also more complex forms may be created as to assist the immediate visual recognition of the produced items, for example heart shape, rhombus, teddy bear for paediatric use.

The bottom side may also have the shape of the backside of a gummy bear, a Santa Claus, an Easter bunny or any other typical foodstuff form, such that a pharmaceutical object may be printed with the shape of a such a typical foodstuff form.

The print base may have recesses being adapted to accept pill blisters. Usually pill blisters are created by vacuum-formed sheets of a suitable plastic. The pharmaceutical objects can be printed inside a positioned blister. Thus time may be saved and contact with anything else than the 3D printer's sterile environment is avoided.

After the printing is complete, a closing device may apply the sealing membrane or film to hermetically seal the blisters.

A further action could be the labeling of the sealed blisters by a labelling device, such as a laser, being connected to the mechanical system.

The system may comprise a print base comprising a thermal conductor, in particular arranged on the side opposite to a side having formatted printing locations. Hence the print base may be heated directly, for example for drying the printed substance.

The system may comprise a temperature sensor for monitoring the temperature of the print base. The temperature sensor may be a contact sensor or a contactless sensor for example an IR or laser sensor.

The system may comprise a temperature control unit, comprising a temperature sensor, a thermostat and/or a thermal switch.

The print base may be made of metal and/or metal alloys like alclad, a corrosion-resistant aluminum sheet formed from high-purity aluminum with surface layers metallurgically bonded to high-strength aluminum alloy core material), like stainless steel varieties, for example type 310-310S, a highly alloyed austenitic stainless steel used for high temperature application. The high chromium and nickel content give the steel excellent oxidation resistance as well as high strength at high temperature, or type 316 excellent for food and surgical uses,—an alloy addition of molybdenum prevents specific forms of corrosion due to its increased resistance to chloride corrosion) and others.

The print base may be made of plastic and/or composite materials. The print base may be made of tempered glass, such as borosilicate glass, 7740 glass. The print base may comprise ceramics, such as glass-ceramics. Glass-ceramics have the fabrication advantage of glass, as well as special properties of ceramics. They can withstand brazing temperatures up to 700 while maintaining properties like zero porosity, high strength, toughness, low thermal expansion, high temperature stability, machinability, high chemical durability, biocompatibility, isolation capabilities, In manufacturing, glass-ceramics are valued for having the strength of ceramic combined with the hermetic sealing properties of glass.

Preferably the print base has a coating, in particular a ceramic glaze coating. The printed pharmaceutical object may detach from the print base and does not stick to the print base.

Many types of coating may be used, for example: ceramic glaze, an impervious layer or coating of a vitreous substance, which has been fused to a ceramic body through firing, silica nano-coating, silver nano-coating, which is anti-bacterial and anti-fungal, titanium dioxide ($TiO_2$), nano-particles, which are sterilizing and have anti-fouling properties.

The base system may also comprise an object remover.

The object remover may be formed by a tilt mechanism, which cants the print base, such that the printed pharmaceutical objects slide down the print base to a collection point, for example into a bin.

The object remover may be formed by moveable extractor pins or gas nozzles being connectable to formatted printing locations of the print base. Each printed object may be ejected from the printing location by the pressure of an extractor pin pricking from a hole in a printing location or by the pressure of blow out of a hole in a printing location.

In a preferable embodiment of the invention the base system comprises a base holder for receiving a print base. The print base may be removed and/or replaced.

Print base with different formatted printing locations may be used in the same system. A print base carrying printed object may be removed from the system and replaced by a fresh print base.

In a further beneficial embodiment the system for 3D printing comprises a mechanical base system capable of moving the print base to one or more directions.

The print base may for example be lifted in a printing level and may be lowered after printing. The print base may also be moved to complete the movement of the mechanical system for moving the print head in order to achieve a full 3D printing also with only a one or two-dimensional movement of the print head.

An advantageous system for 3D printing tablets, granules and capsules has a thermally controlled base with formatted print locations having air ducts for accurately controlling the temperature and humidity of the printed articles.

In a preferred embodiment of the invention the system comprises a chamber, in particular with a door, for establishing a controlled atmosphere. The system is equipped with individual units such as vent filters, ventilation ducts, air filters, an activated carbon filter, an air conditioning system, an air drying system, a vacuum system with a vacuum pump and a head cleaning reservoir.

An advantage of the invention is the ability of the presented system to operate autonomously or in conjunction with a computer to receive orders for 3D printing of granules, tablets and capsules.

The system is preferably controlled by a computer, or a series of computers in order to function. This computer is running on an operational system, for example windows, Linux, IOs etc. and it is provided with all the software necessary to execute it's tasks.

The computer preferably controls all of the system's operations and actions. Every subsystem, device and mechanism may be controlled and made to function by a controller. A controller is a comparative device that receives an input signal from a measured process variable, compares this value with that of a predetermined control point value, and determines the appropriate amount of output signal required by the final control element to provide corrective action within a control loop, a PLC, an EPROM etc.

In many cases the same cables connecting each device to the computer can be the power alimentation source for this device (example USB). The computer may be fitted with all the necessary subsystems to interface with the system's user, such as screen (touch, capacitative, LCD or other), an input method (touchscreen, keyboard, multifunction buttons or other), sound and/or visual allert systems, on/off buttons and any other means of interaction system.

The computer may be equipped with the necessary software to accomplish its functions.

The computer preferably comprises the ability to run auto-diagnosis on every sub-system of the mechanism and inform the user of the need to maintain or repair any part of the system or an imminent failure. This way the maintenance cost diminish and the system's availability increases.

The computer preferably takes care as needed of the calibration of moving mechanisms.

The computer preferably holds the database necessary to select any mixture available and any method suitable to create any product, as well as the form of each product (pill, granule, tablet, suppository etc.).

The computer preferably holds the database of usage statistics and may inform the user of a cartridge containing a particular substance—or mixture of substances—is running low, or even order directly the cartridge needed online streamlining thus the logistics operation.

The database/s necessary for the operations of the system may be stored in the computer's memory and/or at an online position (Internet data storage, remote server, cloud etc.). It may be updated as new products become available (as well as program updates) or can be restored from there if a malfunction occurs.

To achieve this the computer may be provided with a modem (modem, router, etc) connected to the web by cable or wireless technology. Backup of the computer's programs, databases etc. can be provided by flash memory sticks, external hard drives, online data storage etc.

The computer may interact with other devices (external computers, computer accessories like mice, keyboards, webcams, portable hard-drives, microphones, printers, scanners and speakers tablets, smart-phones, screens etc. by cable (USB, DVI, HDMI etc.) or by wireless technologies.

In the case of small systems (desktop sized or portable) the computer could be external to the system (independent).

All the electronic control subsystems—controllers, regulators and other—may communicate directly (by cable) or indirectly by the use of bluetooth, WIFI, IR or other) with the use of an interface device (system to computer) comprising the necessary drivers and program/s (or app/s) to install on the computer used.

Power supply may be provided to all subsystems of the system by a module comprising electric power input (cable/s and/or wireless charger), power converter—example 220v/12v—, battery—or battery packs—, UPS {an uninterruptible power supply, also uninterruptible power source, UPS or battery/flywheel backup, is an electrical apparatus that provides emergency power to a load when the input power source or mains power fails}, an auxiliary or emergency power system or standby generator as well as power outputs (USB or other).

The problem is also solved by a method for producing pharmaceutical objects, such as tablets, granules and capsules, via 3D printing, in particular with a system as described above.

The method comprises the following steps.

At least one pharmaceutical substance is provided in at least one cartridge. The cartridge is placed in a carrier. A fluid connection is established between the cartridge and a print head, such that the pharmaceutical substance may leave the print head through the print head nozzle. The print head nozzle is moved according to a 3D print program and the pharmaceutical substance is dispensed to a print base.

The cartridge may be transferred to the print head and may be moved with the print head.

Preferably a quantity of at least one pharmaceutical substance is dosed from the cartridge to the print head, and the substance is stirred in the print head, in particular a plurality of pharmaceutical substances is mixed.

A pharmaceutical fluid composed and mixed according to a specified recipe may be printed.

A plurality of cartridges, each containing a different pharmaceutical substance, may be arranged in a magazine, and the magazine may be moved with respect to the print head to a position, wherein a selected cartridge is fluid connected with the print head. A quantity of a respective pharmaceutical substance may be dosed into the print head, thereby preparing a pharmaceutical mixture according to a pharmaceutical recipe.

In a beneficial embodiment, the system comprises a plurality of print heads, which are moved independently and which each dispense a substance to a print base. A first print head may be filled with a shell or cover substance, another print head may be filled with a first content substance and a further print head may contain a further content substance, such that pharmaceutical objects within an inner structure may be printed.

The method according to the invention is favourable for situations in which regularly individually designed pharmaceutical objects of similar composition have to be provided, such as in hospitals, in nursing homes, in cruise ships, in naval vessels or in refugee camps.

The storing of the matrix substances is easier than storing a stock for each and every implementation of certain pharmaceutical products.

A reduction of packaging with ecological benefit and cost reduction is achieved.

A print base having formatted printing locations may be applied to a print base system before printing. The pharmaceutical substance may be dispensed on the formatted printing locations.

After printing the print head may be cleaned.

Preferably the method comprises the step of providing at least one substance in at least one cartridge, the substance comprising at least one of a fat mass, a starch, a flour, a gelatine, a sweetener, a natural flavour, an artificial flavour and a colorant.

These foodstuff substances ensure that the printed objects are digestible and tasty.

The cartridge may contain also other foodstuff substances that can be used as excipients like emulsifying agents, stabilizing agents, thickening agents, binders, sweetening agents, sugar coating adjuncts, anti-caking agents, emulsifiers, acidulants, acidity regulators, anti-foaming and foaming agents, antioxidants, bulking agents, food colorings, color retention agents, flavors, flavor enhancers, glazing agents, humectants, preservatives, stabilizers, sweeteners etc.

The additional substances may be provided in separate cartridges, such that a compound material containing pharmaceutical substances and foodstuff substances may be mixed in the print head according to a predetermined recipe.

In a preferred embodiment of the method the pharmaceutical substance provided in at least one cartridge comprises at least one of an antipyretic, an analgesic, an antimalarial drug, an antibiotic, an antiseptic, a psychiatric medication, a mood stabilizer, a hormone replacement, an oral contraceptive, a stimulant, a tranquilizer and a statin.

An antipyretic, for example an acetaminophen, reduces fever, pyrexia or pyresis. An analgesic or painkiller, for example acetaminophens, non-steroidal anti-inflammatory drugs or opioids reduces pain. Antimalarial drugs, for example chloroquine and hydroxychloroquine treat malaria. Antibiotics inhibit bacterial growth. Antiseptics prevent germ growth near burns, cuts and wounds. Mood stabilizers are for example lithium and valpromide. A hormone replacement is for example estrogen or progesterone. Oral contraceptives are for example enovids, "biphasic" pills and "triphasic" pills. Stimulants are for example methylphenidates and amphetamines. Chlorpromazine is an example of antipsychotic medication. Chlordiazepoxide, diazepam, and alprazolam are examples of sedatives and hypnotic medication of the class of Benzodiazepines. Statins are for example lovastatin, pravastatin and simvastatin.

The inventive system and the inventive method may be applied to the formulation of a paracetamol preparation for pediatric use. Children in the age of 6 to 8 years should ingest 250 mg, children in the age of 8 to 10 years 375 mg, children in the age of 10 to 12 years 500 mg, children in the age of 12 to 15 years 750 mg every 4 to 6 hours.

In an example cocoa butter, cocoa powder, sugar and milk or chocolate mass and a quantity of paracetamol suited to the desired drug to be produced, for example 250 mg of paracetamol are dispensed to the print head, mixed and amalgamated. The print head is heated to reach the temperature for melting the ingredients.

The major factor in not using chocolate and other substances which are appealing to the taste, up to now, was the fact that they could be miss-identified as treats and lead to intoxication due to overconsumption.

By the production of such pharmaceutic objects with a 3d printer capable of dosing precisely this peril is practically eliminated, also due to the fact, that the shape of such tablets can be made easy to distinct them, as well as the extremely small quantities can be produced.

On the other hand, substances as chocolate can facilitate the drugs acceptance by those that usually dislike them.

The production of such a tablet will be used as an example for the function of the 3d printing system function.

The first step is to give the system an input that specifies the product desired, for example a 250 mg paracetamol-chocolate tablet for paediatric use.

The system selects the cartridges containing the ingredients (substances) needed and after sequentially removing their protective caps, fills the print head which has been positioned in the filling position. After that the cartridges nozzles are cleaned by a cleaning device and their caps are repositioned. The print head is heated at a temperature of 30 to 35 degrees Celsius to assist melting of the excipients, while the mixing mechanism starts to amalgamate the pharmaceutical substance and the excipients.

The print head is positioned over the print base and starts the print procedure according to the dedicated software's commands. The print base, in turn cools the objects while they are printed so to assist their quick solidification, at a temperature of 20 degrees Celsius. In the same time, the system's airflow and temperature control devices assist the cooling of the tablets under construction.

The procedure ends with the print base delivering the produced items for packaging and the print head and base are thoroughly cleaned and sterilized to be ready for the next system's task. Further excipients that may be used to obtain the desired taste and texture of the tablets, for example cocoa butter, cocoa powder, sugar, milk, white chocolate, caramel, strawberry flavor, black chocolate and other flavors.

These and other objects, features and advantages of the invention will become apparent in the following detailed description.

The invention will become apparent to those skilled in the art with reference to the accompanying drawings in which it is illustrated in an exemplary, non-limiting manner.

Figure 16:
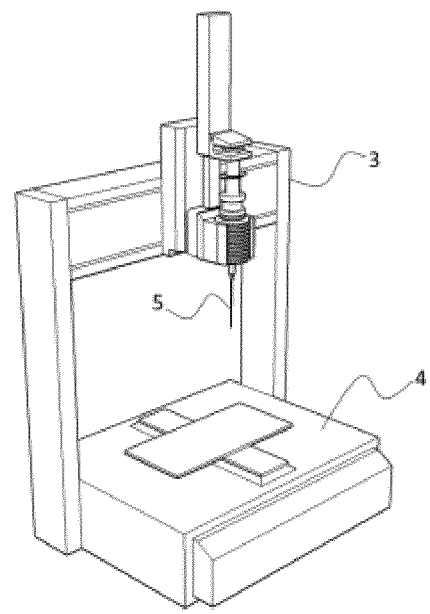
Figure 17:
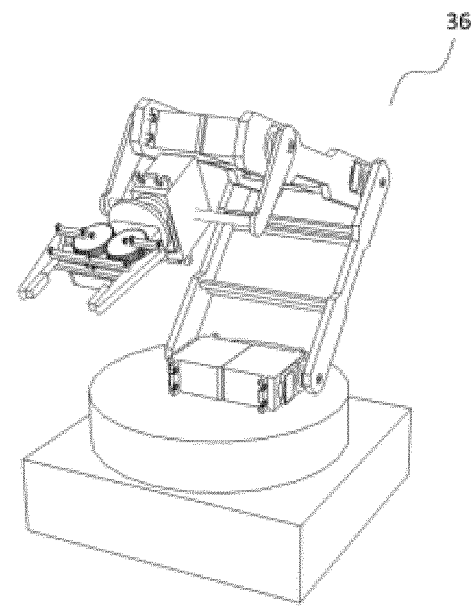
Figure 18:
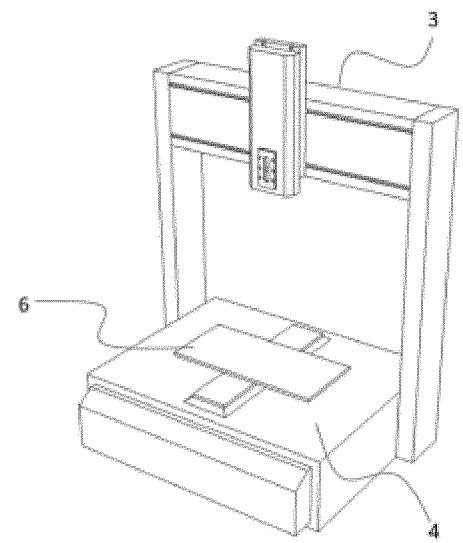
Figure 19:
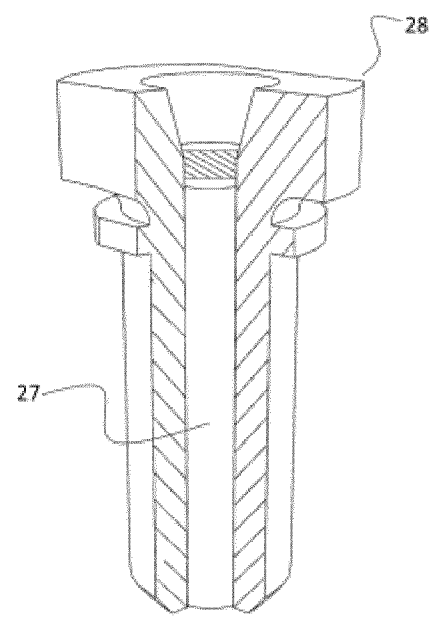
Figure 20:
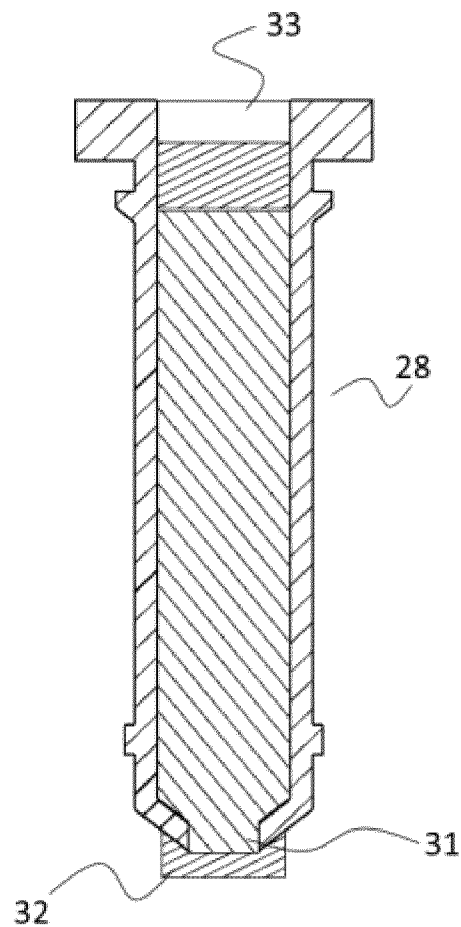
Figure 21:
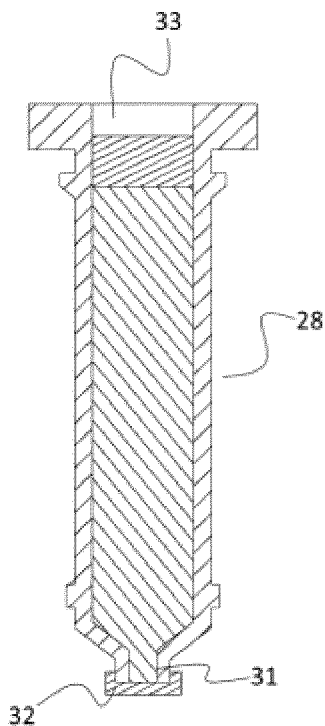
Figure 22:
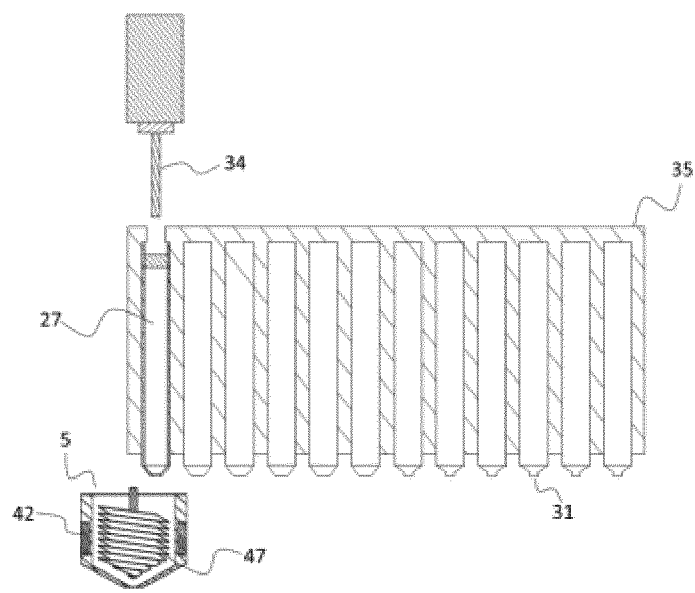

FIG. 16 also shows an alternative embodiment of the 3D printing machine of the illustrated system;

FIG. 17 shows a robotic arm that can be used for the 3D printing of the tablets, granules and capsules through the system of the present invention;

FIG. 18 shows an alternative rack that can be used in the inventive system as 3D printing machine;

FIG. 19 illustrates a partial, longitudinal sectional view of a cartridge used by the present invention for 3D printing of granules, tablets and capsules;

FIG. 20 shows a longitudinal section of a cartridge containing the mixture suitable for each case, while FIG. 21 illustrates an alternative embodiment of a cartridge with a different tip type;

FIG. 22 illustrates an elongated cartridge carrier which can be used in the present system, together with the punch for propelling the mixture.

Figure 23:
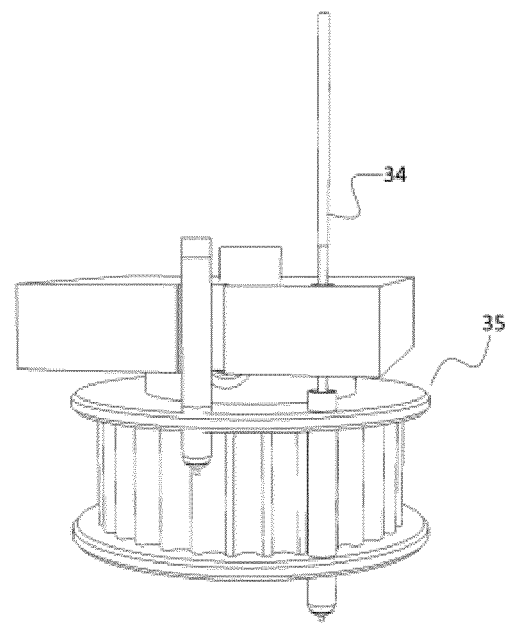
Figure 24:
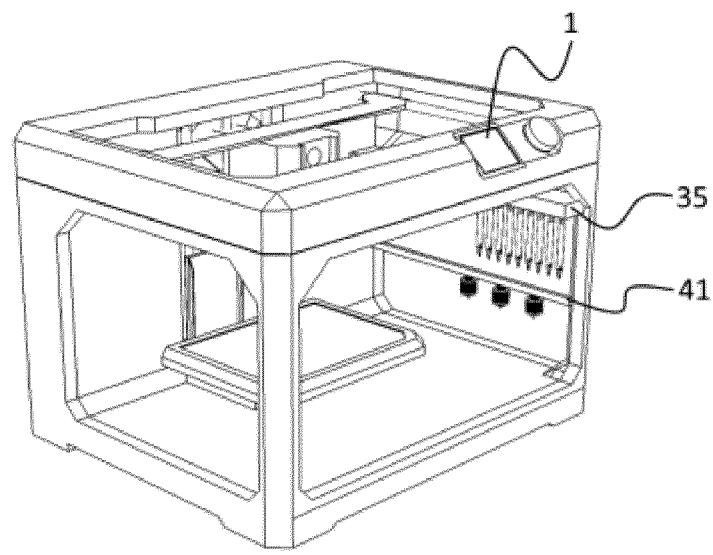

FIG. 23 shows a variant of the cartridge carrier, which is rotatable;

FIG. 24 illustrates an alternative embodiment of the system for producing tablets, granules and capsules by means of 3D printing, in section, in which the arrangement of the cartridges and the print heads may be seen.

Figure 25:
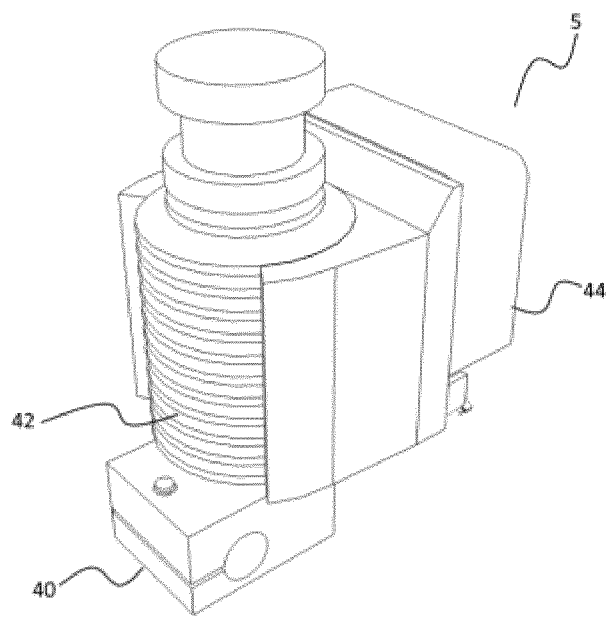

FIG. 25 shows a thermal print head with support base and accessory carrier and

Figure 26:
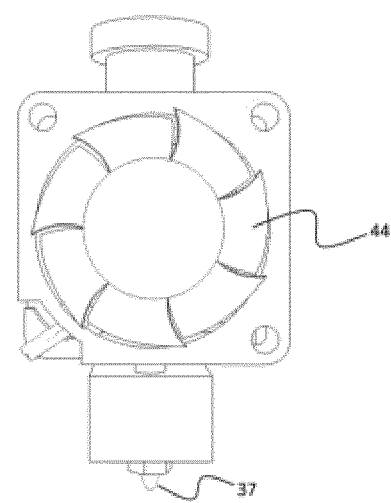
Figure 27:
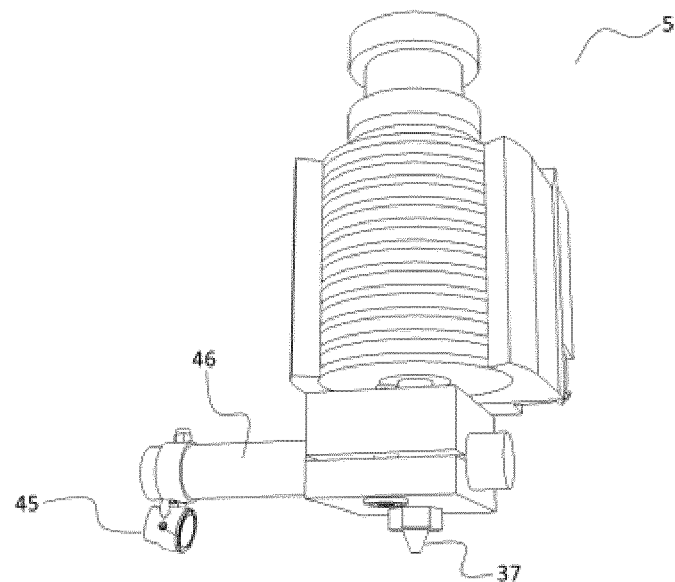
Figure 28:
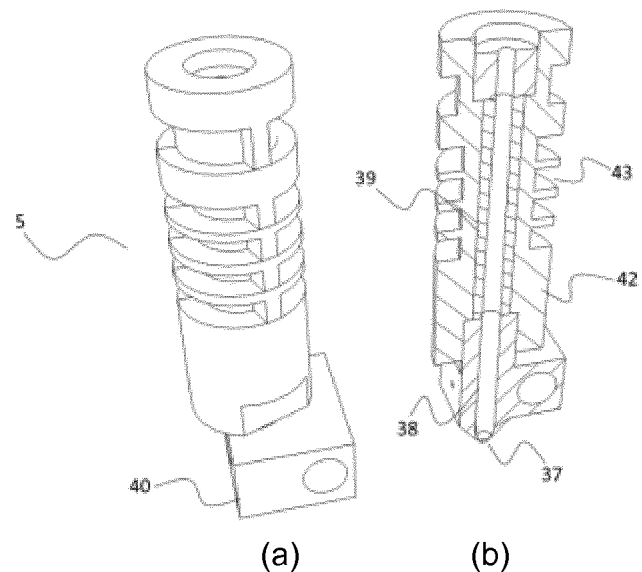
Figure 29:
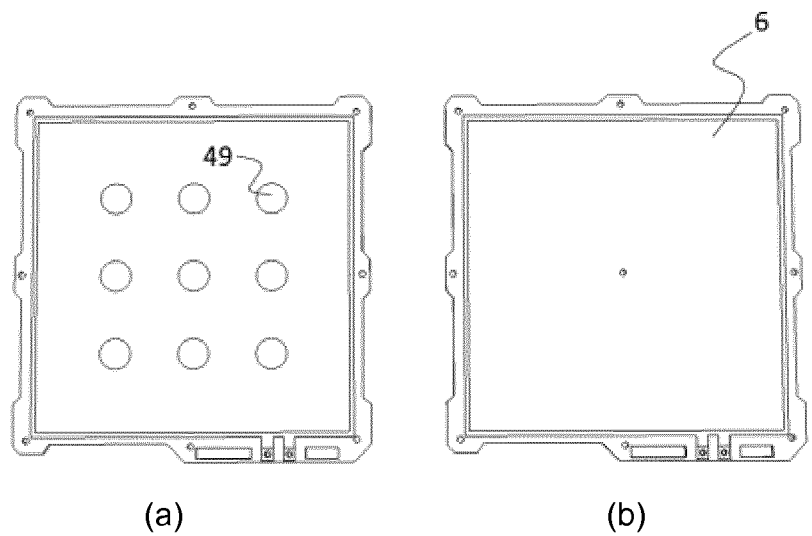
Figure 30:
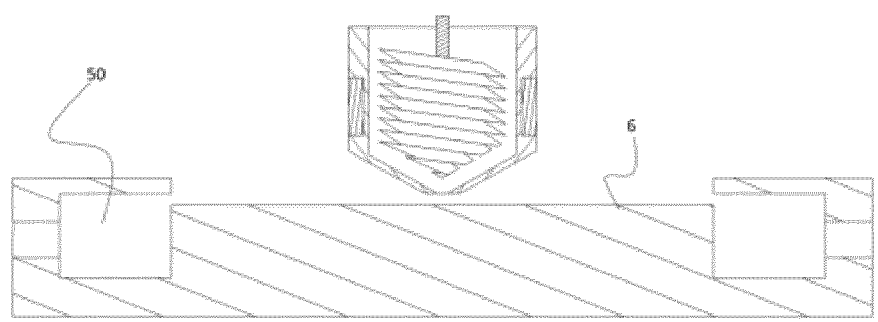
Figure 31:
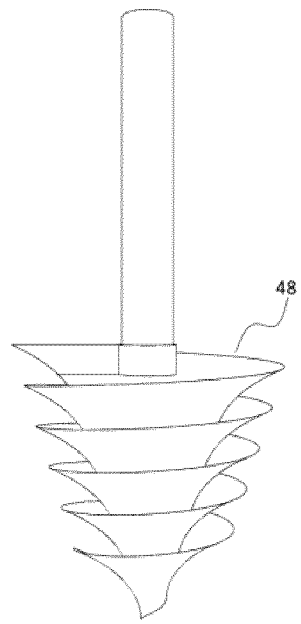
Figure 32:
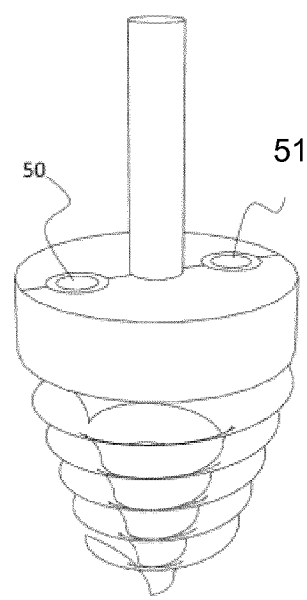
Figure 33:
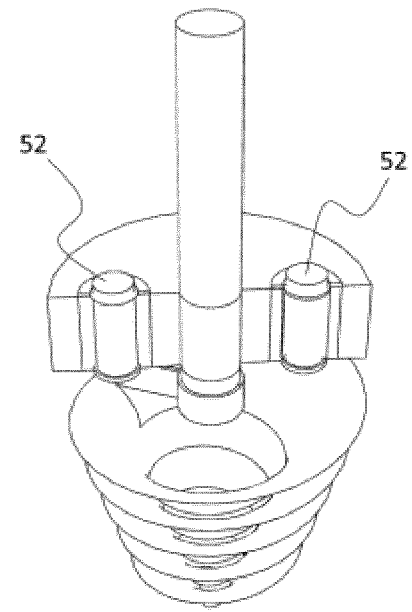
Figure 34:
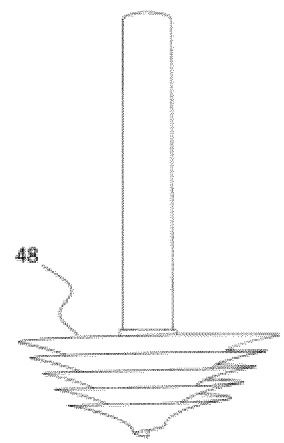
Figure 35:
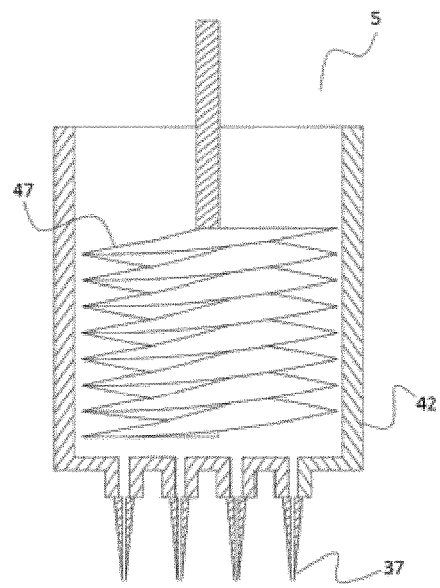
Figure 36:
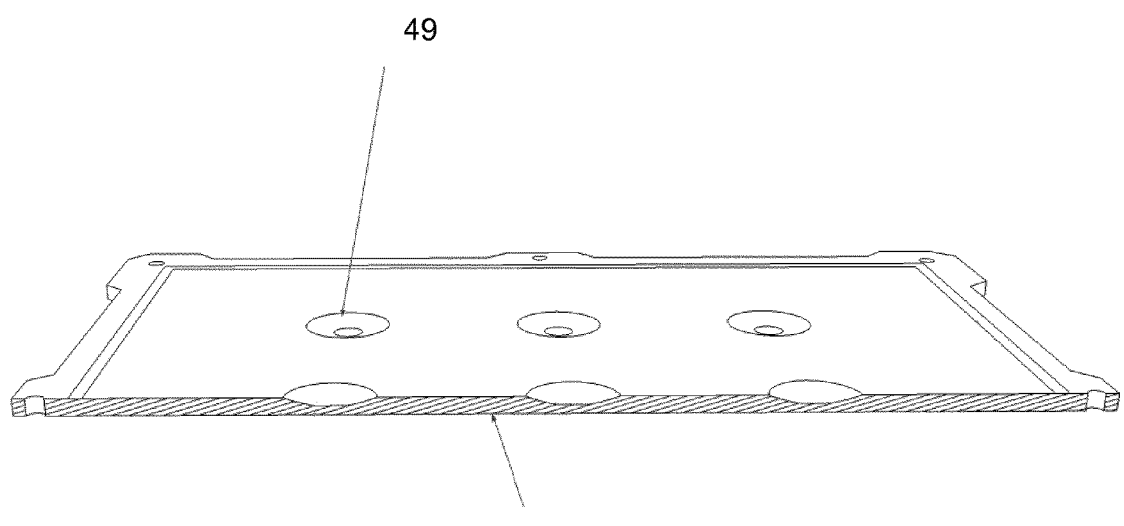
Figure 37:
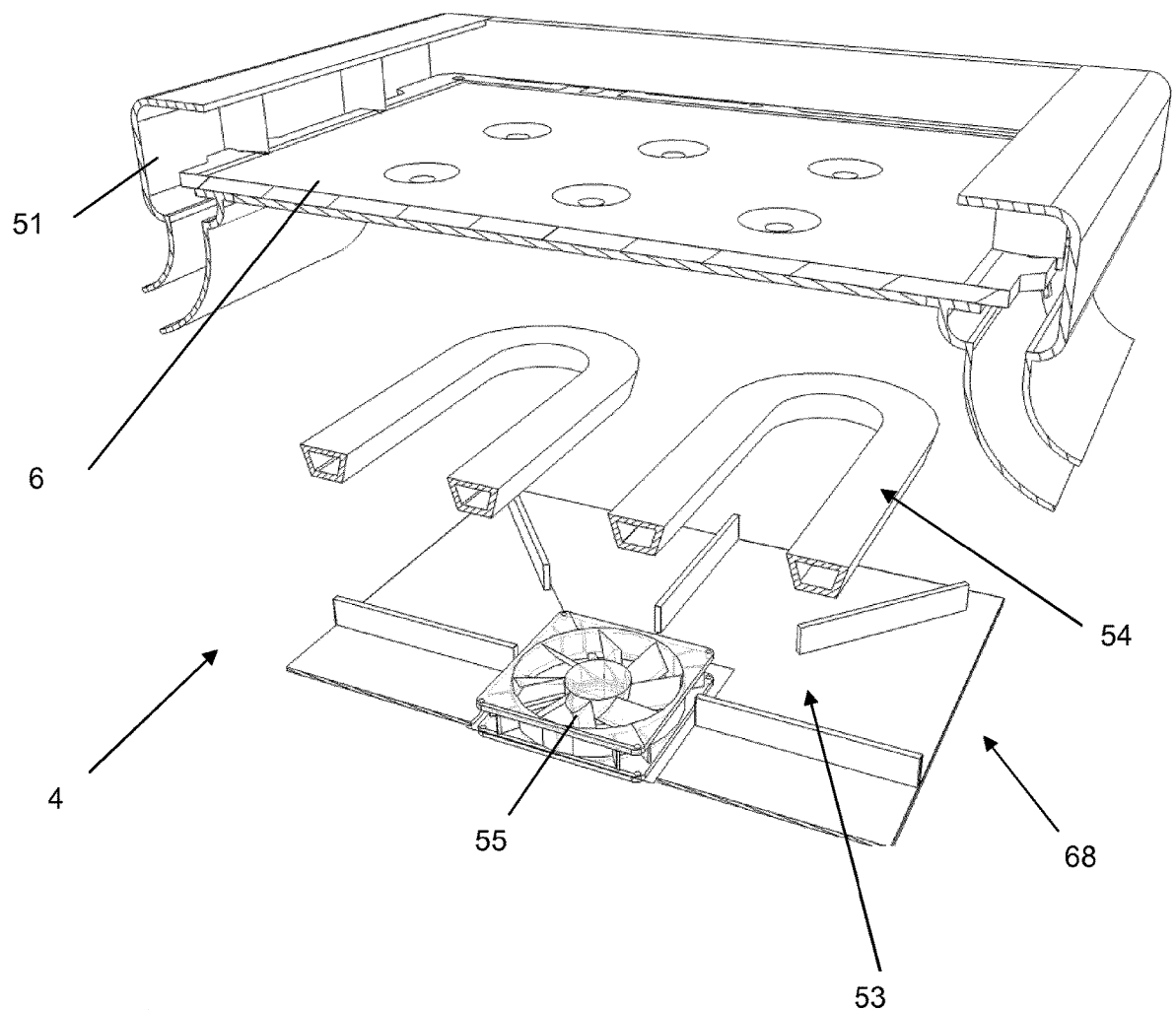
Figure 38:
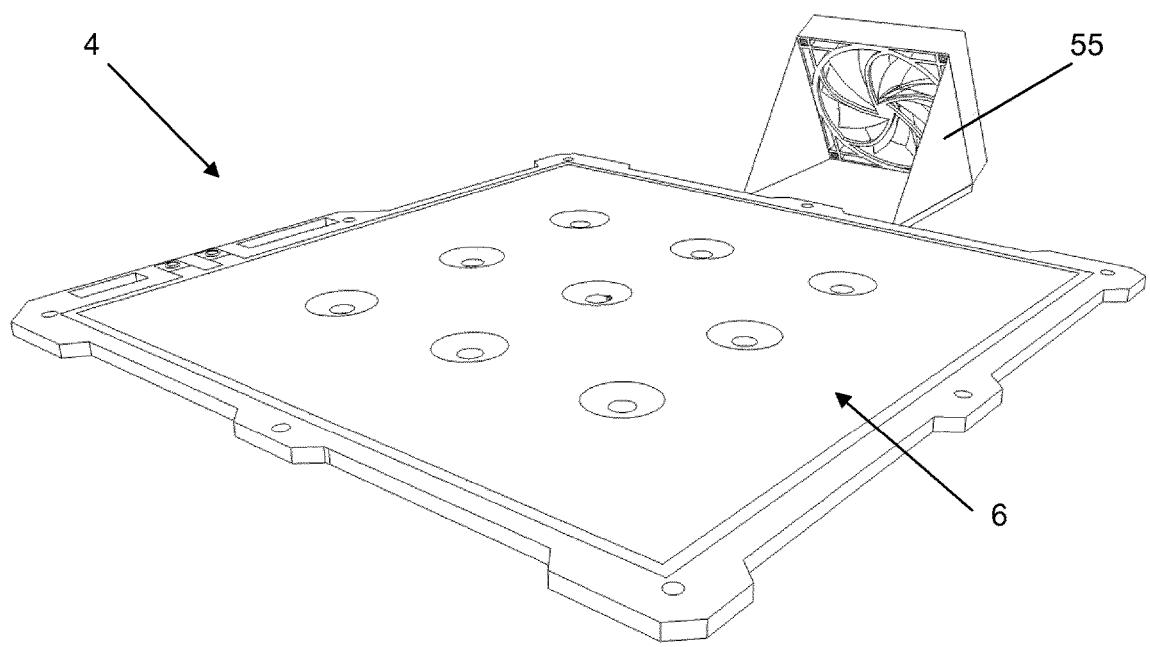
Figure 39:
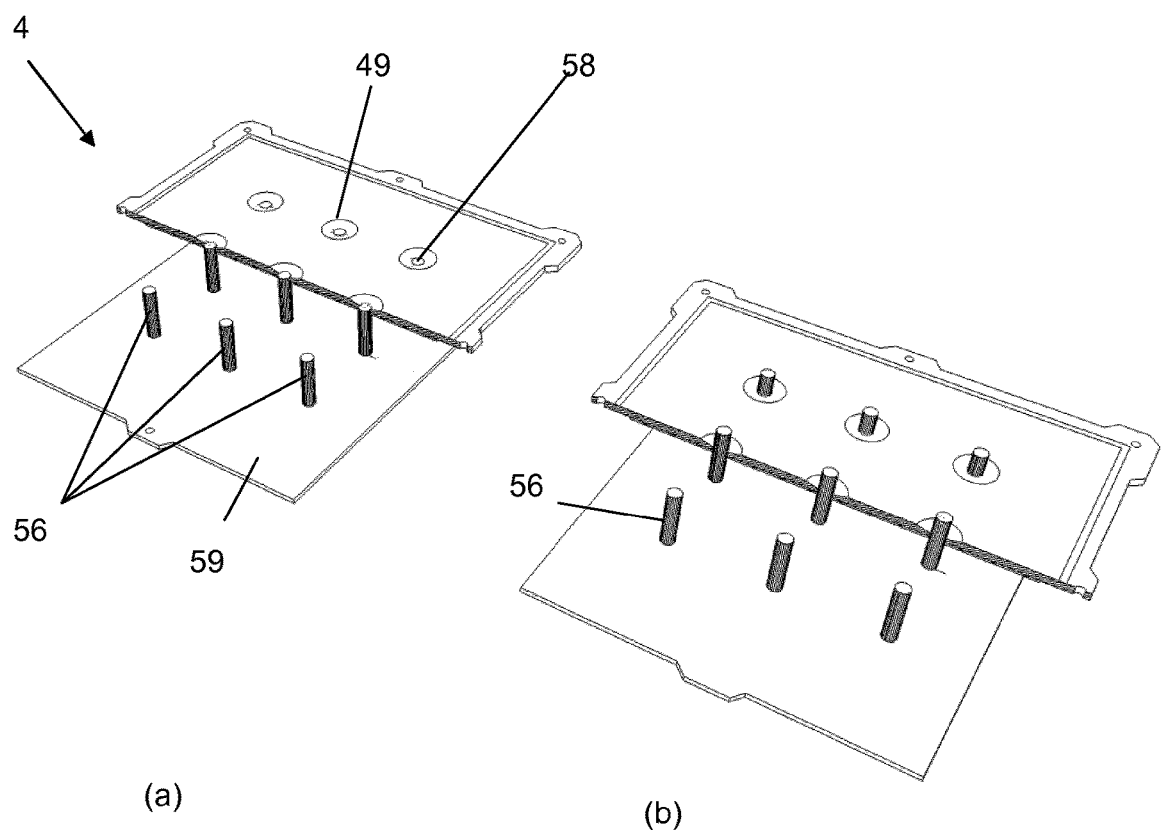
Figure 40:
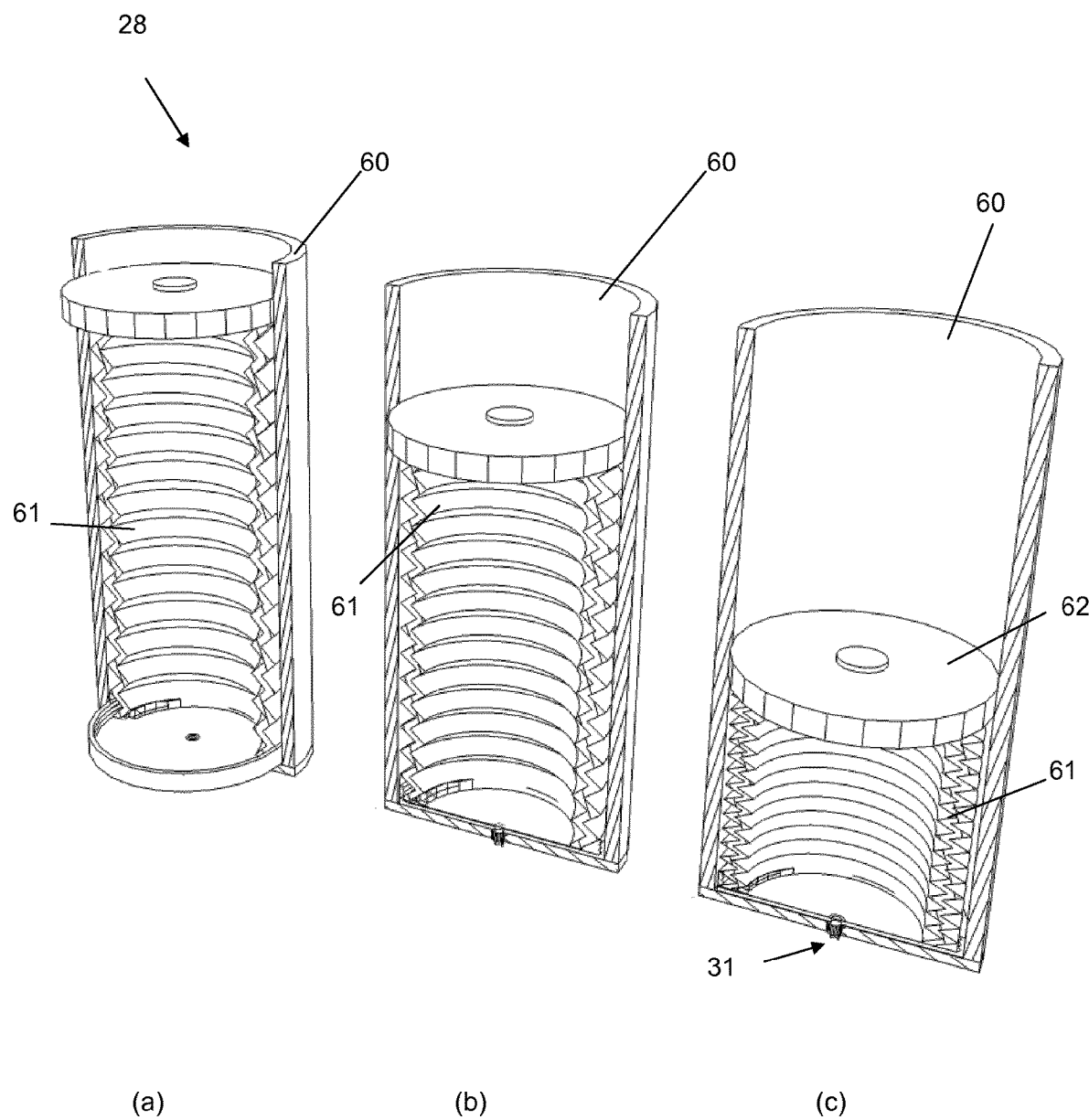
Figure 41:
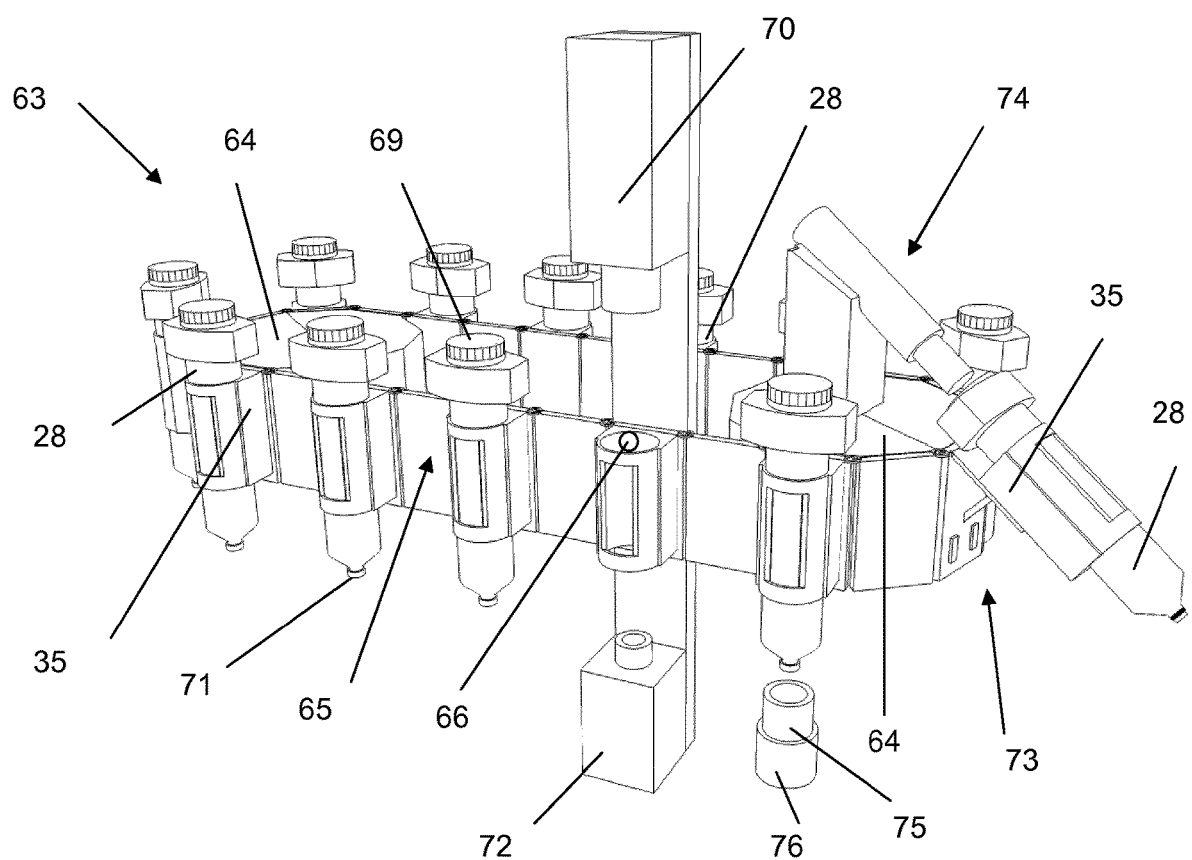

FIG. 26 shows the rear face of thermal head with its respective cooling fan;

FIG. 27 illustrates a thermal head with a feeding device and a Photo-polymerization headlamp on the head carrier;

FIGS. 28 (a) and (b) show a thermal head and its respective section, in which indentations contributing to heat losses are evident;

FIGS. 29 (a) and (b) illustrate thermal print bases, either with formatted printing locations or of a simple type for printing the articles;

FIG. 30 illustrates a base sectional view with air ducts for air circulation;

FIG. 31 shows a collapsible worm screw that can be used in the production system of the present invention;

FIG. 32 illustrates a perspective view of a worm screw with inlets of active substance and outlets of air, respectively;

FIG. 33 illustrates a sectional view of the base of the collapsible worm screw of FIG. 32;

FIG. 34 shows the collapsible worm screw at a time of full collapse;

FIG. 35 is a cross-sectional view of a multi-print head with worm screw that can be used in the 3D print production system of tablets, granules and capsules of the present invention;

FIG. 36 illustrates a print base with formatted printing locations;

FIG. 37 illustrates an example of a base system;

FIG. 38 illustrates a further example of a base system;

FIG. 39 illustrates a print base with extractor pins (a) in passive position and (b) in an extracting position;

FIG. 40 illustrates an embodiment of a compressible cartridge, (a) in a first position, (b) in a second position and (c) in a third position;

FIG. 41 illustrates cartridge carriers arranged in a magazine unit.

Referring now to the accompanying drawings, we will describe exemplary embodiments of the system for producing tablets, granules and capsules by means of 3D printing, in order to make understandable the operation thereof.

Figure 1:
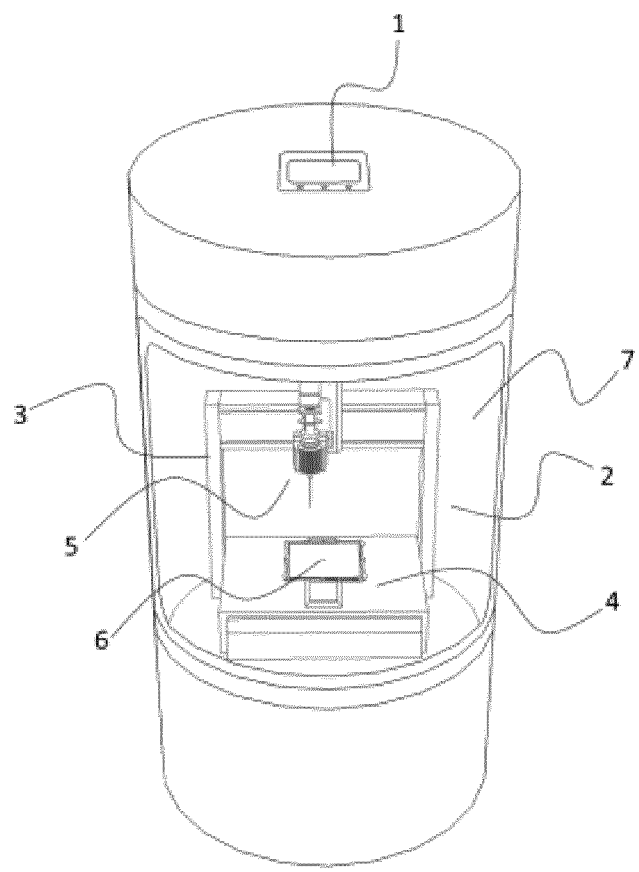
FIG. 1 shows a perspective sketch of an illustrative basic embodiment of the 3D printing production system of tablets, granules and capsules.
Figure 2:
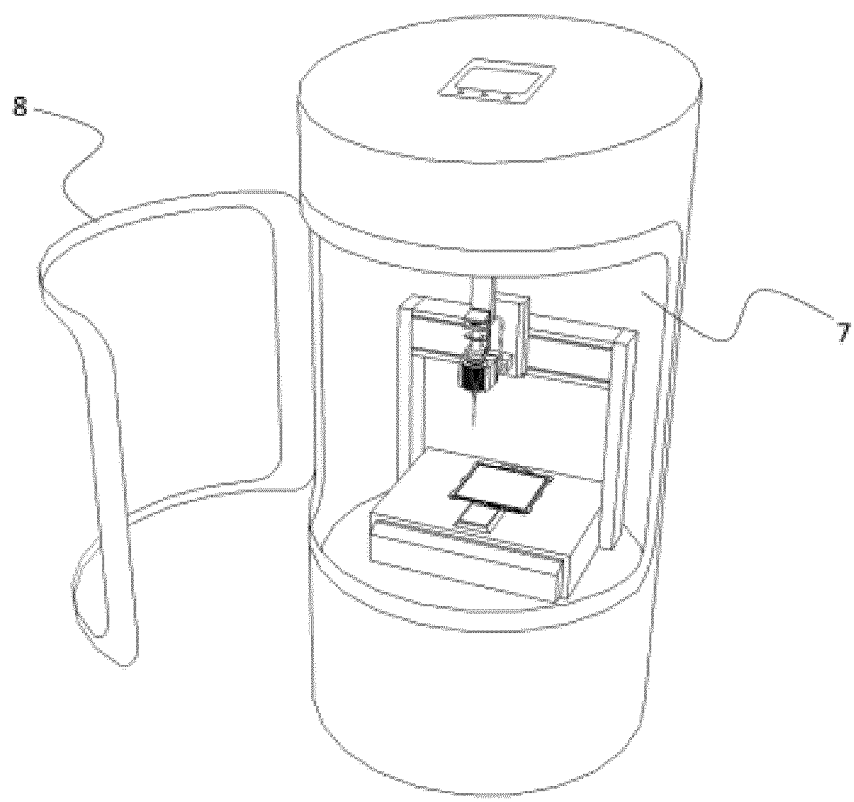
FIG. 2 shows a perspective sketch of the basic embodiment of the system for producing tablets, granules and capsules by means of 3D printing, with its door open.

The basic structure of the system is shown in FIG. 1 and comprises a display 1 with keys or touch buttons, from which the user can enter the necessary data and monitor the displayed indications during the system operation. It also comprises a 3D printing machine 2 which has a mechanical system 3 comprising a mechanical arm, movable in one or more directions, a base system 4 which can be fixed or mechanically movable in one or more directions and a print head 5 which dispenses the mixture, depending on the instructions received from software, for the 3D printing of tablets, granules and capsules on the print base 6. The 3D printing machine 2 is located within a chamber 7, which is closed by a door 8, FIG. 2, to create a controlled environment during printing.

Figure 3:
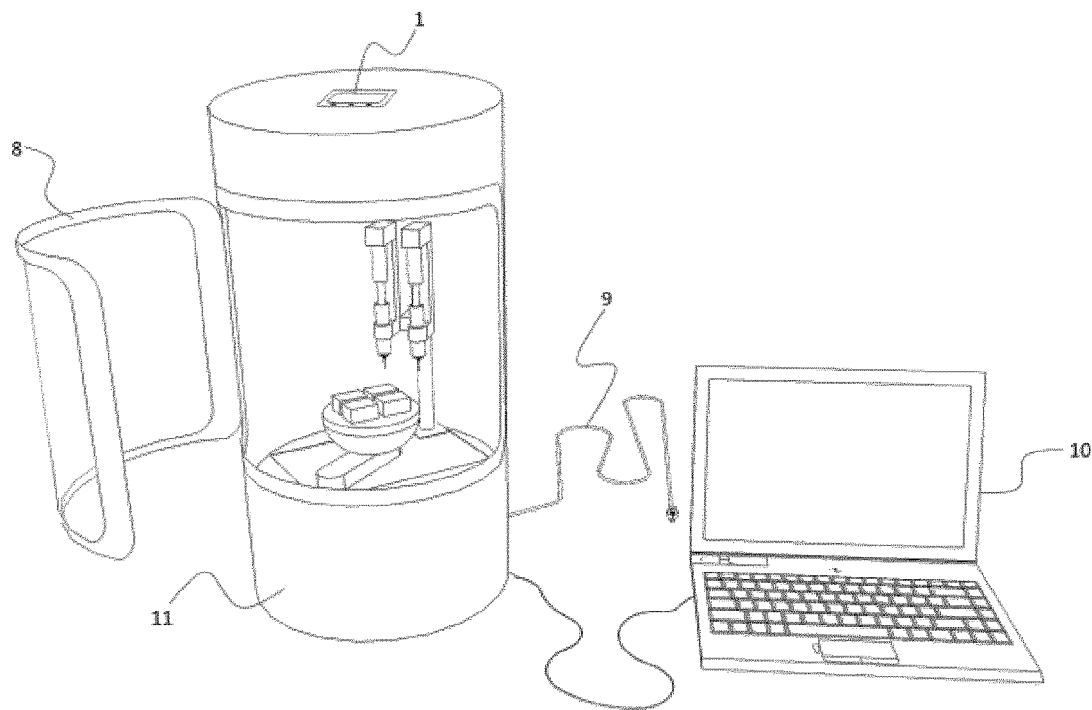
FIG. 3 shows a perspective sketch of an exemplary embodiment of the production system, as it is connected to a computer, the dual print head of the system is also displayed.

The system for producing tablets, granules and capsules by means of 3D printing of the present invention is further provided with a power cable 9, FIG. 3, and can be connected to a computer 10. This connection can be wired or wireless. However, the system itself may have a built-in computing unit on the base 11 so that no connection to an external computer 10 is required for its operation.

Figure 4:
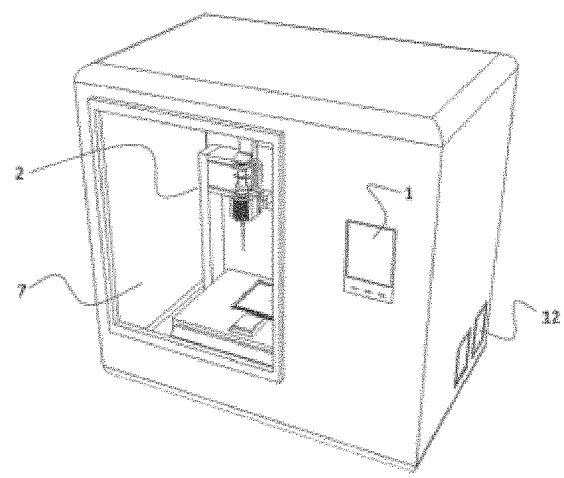
FIG. 4 illustrates shows a perspective sketch of another exemplary embodiment of the system for producing tablets, granules and capsules by means of 3D printing.
Figure 5:
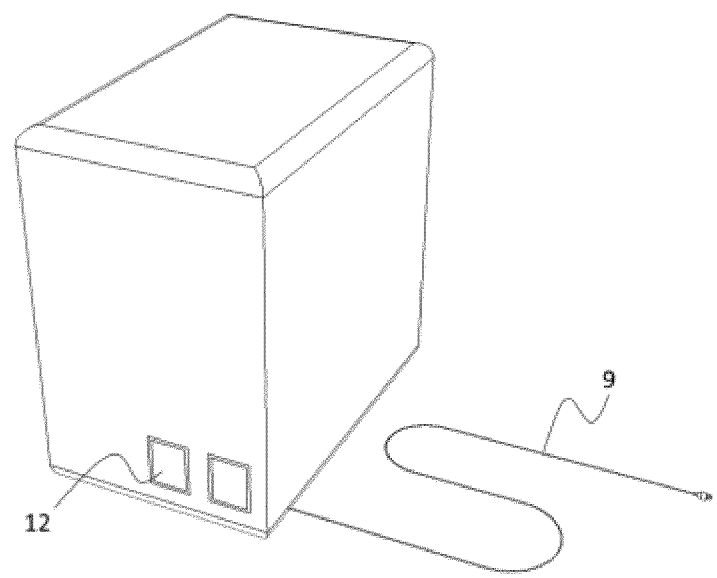
FIG. 5 shows a rear perspective view of the system for producing tablets, granules and capsules by means of 3D printing, where how supply is carried out is also displayed.

In an alternative embodiment of the invention, the system for producing tablets, granules and capsules by means of 3D printing may be in the form of FIG. 4 similarly including a display 1, a power cable 9, FIG. 5 and a printing chamber 7, in which there is a 3D printing machine 2.

Figure 6:
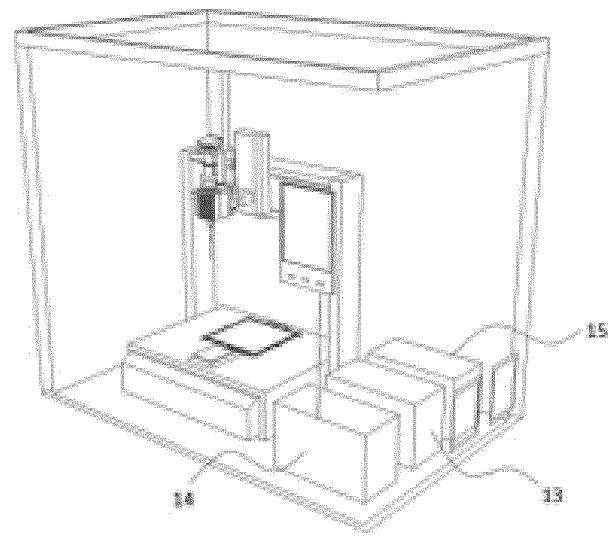
FIG. 6 shows in section the embodiment of the tablet, granule and capsule production system by means of 3D printing, also showing the individual components thereof.

However, it further has one or more ventilation ducts 12 which contribute to the proper circulation of air inside the printing chamber 7. The system is also equipped with an air filter 13, FIG. 6, for cleaning the circulating air, which can be detachable for washing or replacing it when required. A computer unit 14 and a supply unit 15 of the entire system can make it completely autonomous.

In yet another alternative embodiment of the invention, the system for producing tablets, granules and capsules by means of 3D printing, may have additional functional elements making it capable for use in more complex applications.

Figure 7:
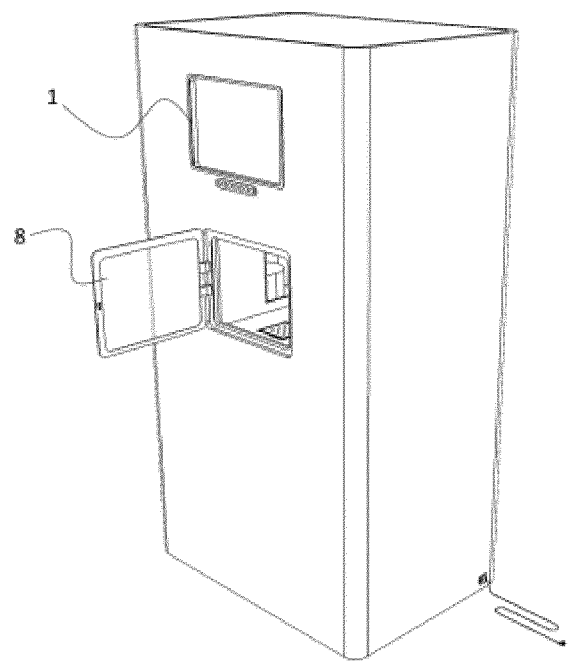
FIG. 7 shows in perspective view yet another embodiment of the tablet, granule and capsule production system, via 3D printing, with its door open.
Figure 9:
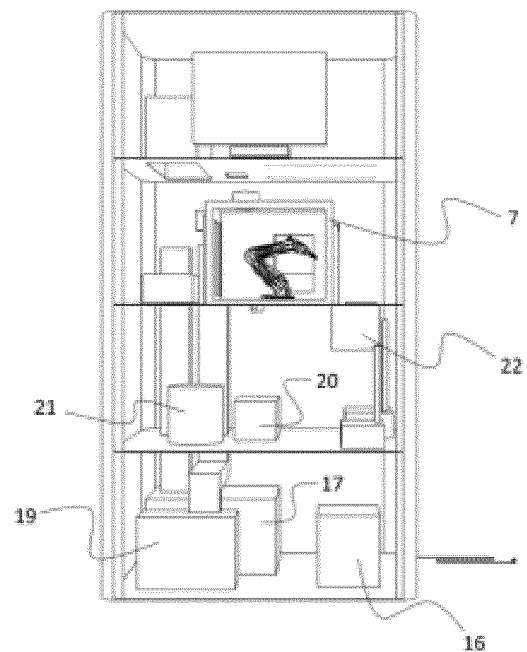
FIG. 9 shows a sectional front view of the system, where the individual components thereof are shown.
Figure 10:
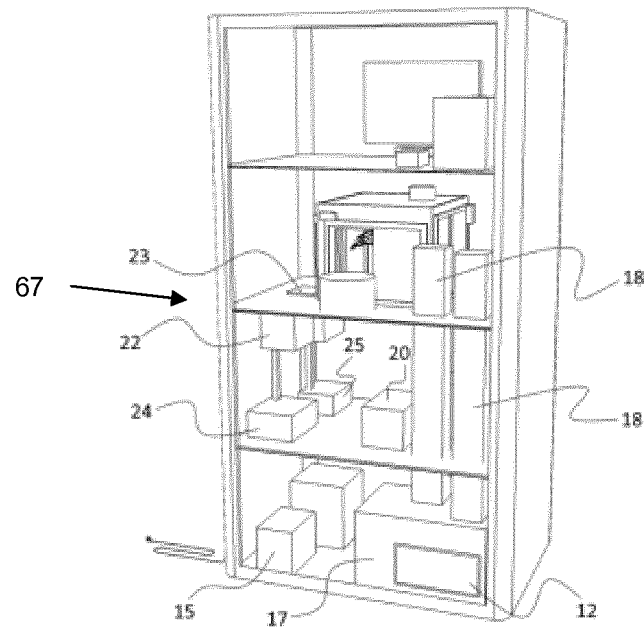
FIG. 10 shows in section the rear view of the system of FIG. 7.

The system has a display 1, FIG. 7, and a door 8 and furthermore has a power supply unit with voltage stabilizer 15, FIG. 10, as well as an uninterruptible power supply 16, FIG. 9, allowing for the uninterrupted operation of the system.

In order to control and maintain the appropriate atmospheric conditions in the printing chamber 7 as well as in the system as a whole, there is an air conditioning and air drying 17 system, while the ventilation ducts 12 allow for the ambient air to enter when this is required. The air conditioning and air drying system 17 is connected by means of one or more air supply and return ducts 18 to the printing chamber 7 and generally to the interior of the system so that when actuating helps in developing the appropriate conditions.

Figure 8:
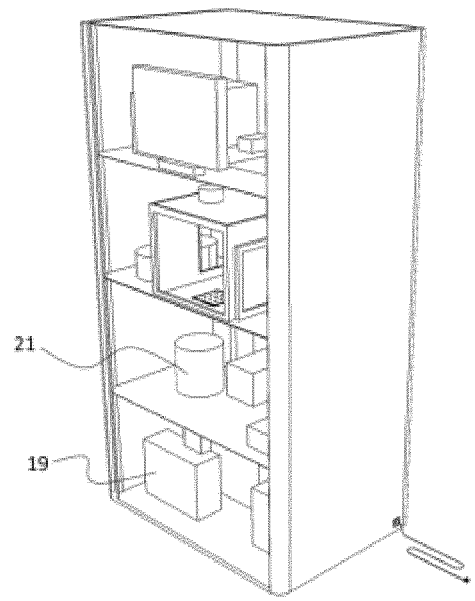
FIG. 8 shows in section the perspective illustration of the above exemplary embodiment of the system.

The system also has an activated charcoal filter 19, FIG. 8, for absorbing carbon dioxide and other harmful substances from the circulating air, while a vacuum pump 20 and a negative pressure container 21 contribute to the creation of a vacuum or the appropriate pressure conditions, depending on the requirements.

Figure 12:
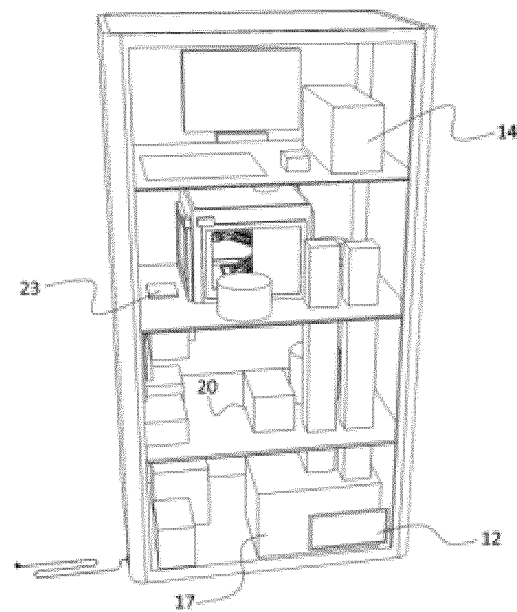
FIG. 12 shows, in yet another embodiment, the rear view of the system of FIG. 7.

The system may have a cleaning unit 67 comprising a wash tank 22 inside which the print head 5 is washed and cleaned through a wash tank port 23, FIG. 12. In this case, it has a reservoir 24 for the cleaning liquid of the print head 5 and a filtering system 25 for the head cleaning liquid, ensuring that it will be free from any debris after cleaning the print head 5.

The cleaning liquid may be selected from the following examples.

Organic acids, surfactant compounds, corrosion inhibitors, which can be used with precious metals, stainless steel, non-ferrous metals, chromium-plated metal, glass, plastics, semi-precious stones, quartz, ceramics for the removal of lapping pastes, oxide films and annealing colors, for example hydroxyacetic acid.

Acids, solubilizers, wetting agents for removing oxide films from non-ferrous metals with-out corroding metal surfaces and/or for removing lime deposits, for example phosphoric acid.

Alkalines, complexing agents, sequestering agents, solubilizers, surface active compounds, surfactants for removing synthetic resins, mixtures of amorphous resins, polish and abrasive, for example KOH-based or NaOH-based detergents residues, in particular with bactericide and virucidal activity.

Neutral pH cleaner with pH 6-9, for cleaning aluminum and other soft metals, for example NpH sterile or neutral detergents.

The cleaning liquid preferably is phosphate and chlorine-free.

After 3d printing the print head preferably passes prefiltered drying air which is heated shortly before entering the cleaning unit. The air may be filtered again through a suitable filter, as for example, a HEPA H13 filter is required in Europe. The detergent can be used with ultrasonic or spray technology or as a foam detergent.

Figure 11:
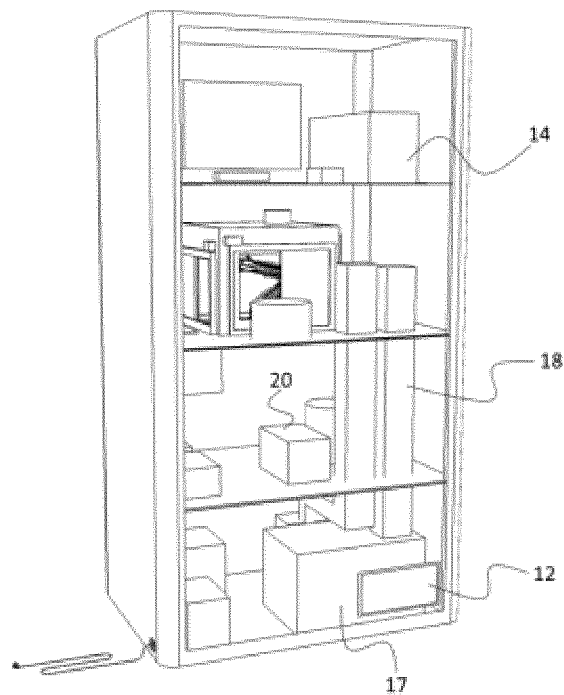
FIG. 11 is a sectional view of the rear view of the above system at a different angle to make visible further details thereof.

The system will have the corresponding computing unit 14, FIG. 11, for processing and executing commands, as previously reported.

Figure 13:
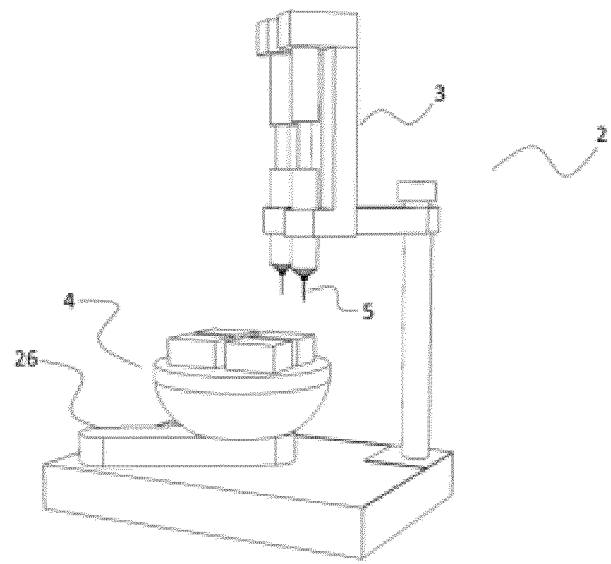
FIG. 13 shows an exemplary embodiment of the 3D printing system machine equipped with a dual print head and a movable mechanical base.
Figure 15:
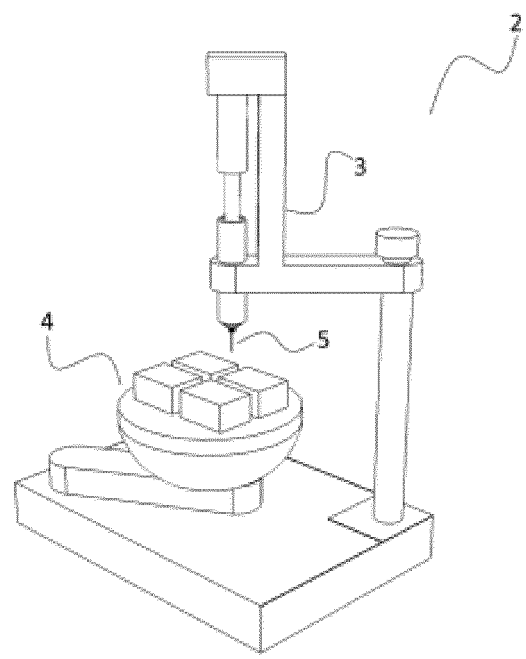
FIG. 15 illustrates another alternative embodiment of the 3D printing machine with an arm movable to one or more directions, with a print head and a base movable in one or more directions.

Every system has, as mentioned, a 3D printing machine 2, FIG. 13, which has a mechanical system 3 which ends in one or more print heads 5 for printing on a base system 4. The base system 4 may be fixed or movable in one or more directions, depending on its axis' degrees of freedom 26. Likewise, in alternative embodiments of the invention, the mechanical system 3 may move in one direction, for example up and down, FIG. 15, in two directions, for example up and down and right-left, FIG. 16, or even have a different shape, FIG. 17, possessing more degrees of freedom.

For example, the 3D printing machine 2, FIG. 18, has a base system 4 with a base 6 moving in 2 dimensions and a mechanical system 3, similarly movable in 2 dimensions. 3D printing of tablets, granules and capsules requires one or more mixtures of active substances and substances with plastic (bonding) properties, depending on the finished product to make.

Figure 14:
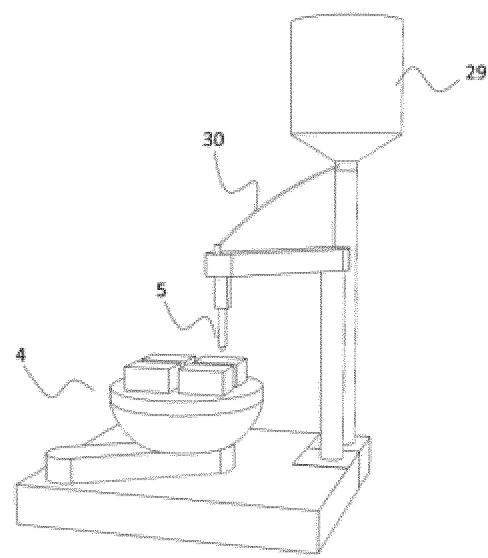
FIG. 14 shows an alternative embodiment of the 3D printing Machine of the illustrated system, which is capable of continuously delivering a mixture for printing.

The mixture 27, FIG. 19, which may be exclusively an active substance, exclusively a plastic or a bonding or a combination thereof, may be in liquid form within a cartridge 28, which is fed in the print head 5 or may be constantly provided thereto via a container 29, FIG. 14, which is connected by a fed line 30, for example a dispensing tube, with the print head 5.

The number of containers 29 connected to the print head 5 may be higher than one. Further and alternatively, the cartridge 28 may be permanently attached to the head 5 and singly replaced after it is emptied. In another alternative embodiment the mixture 27 may also have the form of filament.

Since the viscosity of the mixtures used varies depending on the manufactured product, the cartridge 28 has different cross-section ends. It may therefore have a wide cross section at the end 31, FIG. 20, or have a narrower cross section, FIG. 21. To close the cartridge 28 underside, a cap 32 may be used, the use of any other appropriate closure whatever not excluded. The upper side of the cartridge 28 has a downwardly movable lid 33 which is urged by a punch 34, FIG. 22, to provide the mixture 27 to the print head 5. The lid 33 may be equipped with a suitable device, such as a radio frequency identification system, to enable the punch 34 to determine its exact location, as well as relevant cartridge information 28.

The cartridges may be provided at their nozzle with a valve to avoid spillage, dry-outs etc. A valve is a device that regulates, directs or controls the flow of a fluid (gases, liquids, fluidized solids, or slurries) by opening, closing, or partially obstructing various passageways. Valves are technically fittings, but are usually discussed as a separate category. In an open valve, fluid flows in a direction from higher pressure to lower pressure.

The simplest, and very ancient, valve is simply a freely hinged flap which drops to obstruct fluid (gas or liquid) flow in one direction, but is pushed open by flow in the opposite direction. This is called a check valve, as it prevents or "checks" the flow in one direction. Modern control valves may regulate pressure or flow downstream and operate on sophisticated automation systems. These valves may be spring loaded, elastic—made of silicon or other material with similar characteristics of elasticity—having a hole or a cut (straight, cruciform etc) to allow the exit of the material from the cartridge when pressurized by the shaft on the plug. In this case the protective cap of the cartridge's nozzle can be fitted with a small needle. Alternatively at least one blade may be used in the case of cuts on the valve suited to their form, for example cruciform.

The valve may be of a different type for example a doser-type devise to control the flow if the material included in the cartridge is of a dry (solid) type, such as powders, granules conglomerates etc., or an on/off valve (shutter valves, ball valves, pin valves etc.) for use with liquids. The valves can be pressure inserted at the cartridges nozzle or glued. In the case of solid materials the valve mechanism may form the lower part of the cartridge itself.

Every system may be equipped with more than one cartridge 28 with the same or different mixture 27 and with the same or different end 31.

The cartridges 28 are arranged in carriers 35, which may be elongated or even rotatable, FIG. 23. The carriers 35 are mechanically driven by a servomotor or other suitable device, leading the appropriate cartridge 28 into a loading position so that the punch 34 pushes the appropriate amount of mixture 27 into the print head to start the process. The carriers 35 may be located within the 3D printing machine 2, FIG. 24, and led over the base system 4 to start the process or may be firmly positioned at a point from which an arm 36, FIG. 17, receives a cartridge 28 at a time. The size of the carriers 35 and the number of cartridges 28 this may carry is limited only by the available space of the system.

The cartridges may vary in size or shape depending both on the production method. They may be bigger for mass production, for example in a factory, medium sized for pharmacies and hospitals or smaller for desktop or mobile use.

The cartridges as said are preferably created using materials that does not interact or contaminate in any way the included substance (example: oxidation of metal in contact with aqueous or alcohol solvents).

Such materials comprise a vast array of metals like stainless steal, aluminium alloys, and in any case techniques that form a membrane like coating can be used to insulate the contained substance from any metal that could potentially harm it so in theory any metal could be used. As examples of such techniques we could mention: electroplating, spray or dip painting, ceramic coating or even internal extrusion of a suitable plastic membrane.

Such materials comprise a vast array of plastic materials and in this case care must be given on the avoidance of contamination which may come by reaction (example alcohol solvent and some types of polyethylene plastics) or by release of volatile gases and/or oil substances contained in the plastic itself (example some polyethylene, polyurethane and polyester materials).

In any case a huge variety of plastic materials are available to use such as epoxy, some nylons, polyethylenes and even greater number of composite materials (example nylons with glass micro-spheres created by injection molding or epoxy combined with ceramic micro-spheres).

In the case of plastics, techniques mentioned before may come in use either to further enhance defense of the contained substances or to allow the use of non suited materials by forming an internal layer of protective material suited for the job (example dual extrusion of PET or PETG and ABS. Such techniques are often used in plastic made, disposable, water and soda bottles). Harder or not-extrudable plastics can be rendered temporarily electro-conductive and thus plated or they may simply be sprayed or dipped to form the protective layer using a suitable material. In any case glass and ceramics may be used.

Preferably the cartridges incorporate in their body various methods of identification (RIFD or other chip, barcode or other) which provide an interface with a reading unit 66, see FIG. 41, on the carrier or on a storage container. This info allows the system to recognize the ingredients contained, such that a correct volume may be chosen, or to recognize the shelf-life of each product, the remaining volume in each cartridge, the frequency of use and other. This information can be used as statistics to optimise production and if needed to automate the supply chain by ordering of replacement refills in time.

The print head 5 is the device intended to apply the necessary amount of mixture 27 to produce the corresponding granule, tablet or capsule. The print head 5 is provided with a nozzle 37, FIG. 26, from which the mixture 27 is supplied and a print head body 38, for example formed as a cylinder, with an envelope 39. It further has a support 40, FIG. 28 (a), through which it is held either in a head carrier 41, FIG. 24, or in an arm 36.

The print head may be a thermal one, FIG. 25, in order to improve the temperature control of the mixture 27. For this purpose, it has a heated body 42 with indentations 43 which contribute to heat losses, and can also be provided with a cooling fan 44, FIG. 26, on its rear side, further improving the temperature control.

In yet another alternative embodiment, the print head 5 may be provided with an energy emitter 45, in this example a photopolymerization headlamp, FIG. 27, supported on an arm 46, to be used for mixtures 27 requiring its presence.

In another alternative embodiment, the print head 5 may have a liquid nitrogen spray nozzle for direct cooling the printed article.

In an alternate embodiment of the invention, the print head 5 may be provided with a stirring and/or discharge tool 47, in this example a worm screw, FIG. 22, which is rotated continuously or intermittently by means of a servomotor and which shakes the mixture within the print head 5. In this way the mixture 27 will retain the necessary viscosity, depending on the application to be used.

In yet another alternative embodiment of the invention, the worm screw 47 may have a collapsible head 48, FIG. 31, which, in addition to stirring the mixture 27, compresses it appropriately by removing the air. To do this, it has a hole 51 at the top of the head 48, FIG. 32, from which the solvent, the active drug substance or the mixture in general are introduced and a hole 50 from which the air is discharged by compression. The holes can be closed by stoppers 52, FIG. 33 when their use is not required. The collapsible head 48 can be made of stainless steel, thermoplastic materials, and composite materials, such as para-aramid synthetic fibre or memory metals, FIG. 34.

In a further alternative embodiment of the print head (5), this may have both a worm screw 47 with or without a collapsible head 48, with or without a heated body 42 and with more than one nozzle 37, FIG. 35, so that 3D printing takes place at a faster rate.

The 3D printing of the tablets, granules and capsules is carried out as mentioned above on a base 6, FIG. 29 (b), which is on the base system 4.

The print base 6 may also be temperature-controlled, and it may also have formatted printing locations 49, FIG. 29 (a) and FIG. 36, for forming the tablet, granule or capsule, by applying the mixture 27.

Upon completion of 3D printing, the articles are removed from the base 6 and the base is repositioned on the base system 4 for later execution of the process. The base 6 may further have air ducts 50, FIG. 30, which allow for natural or forced air flow on the base 6, in order to reduce the evaporation of the moisture content in the produced articles.

FIG. 37 illustrates an example of a heatable base system 4. The print base system 4 comprises a temperature control system 68 with air ducts 53 and channels 54 for guiding a tempering agent, as well as a fan 55.

The print base 6 is removeably held by a print base holder 57 and may be pushed in and pulled out.

FIG. 38 illustrates a further example of a base system 4, wherein a fan 55 is arranged laterally from the print base 6.

FIG. 39 illustrates base system 4 comprising extractor pins 56. In FIG. 39 (a) the extractor pins 56 are in a passive position, closing holes 58 in the formatted printing locations 49. The extractor pins 56 are arranged on a plate 59 which may be moved vertically. When the plate is moved upwards, the extractor pins 56 are in an extracting position, FIG. 39 (b). The extractor pins 56 reach out of the holes 58 and may printed matter (not explicitly shown) out of the formatted printing locations 49.

FIG. 40 illustrates an embodiment of a compressible cartridge 28, (a) in a first position, (b) in a second position and (c) in a third position.

The cartridge 28 may comprise a double body: an external cylindrical shape hard body 60 and an inner container 61 made from compressible material. On the upper part there is a plug 62 which may be press downwardly to expel a printing substance (not explicitly shown) out of a lower end 31 of the cartridge 28.

The cartridge 28 may be used as print head, when the cartridge is arranged on the mechanical system and when there is a printing nozzle (not shown) mounted to the lower end 31.

FIG. 41 illustrates cartridge carriers 35 arranged in a magazine unit 63. Each carrier 35 may accept a cartridge 28. The magazine unit 63 comprises rotating actuators 64 and a belt 65 for moving the cartridges 28. Each carrier 35 comprises a reading unit 66 for reading a cartridge 28 identification.

When a cartridge 28 is needed for filling material into the print head (not shown in the figure), the upper cap 69 is removed by an upper-cap remover 70. The carrier 35 being positioned near the upper-cap remover 70 is shown without a cartridge for clarity. Also the lower cap 71 is removed by a lower-cap remover 72. The cartridge is then moved to a dispensing place 73, where the carrier 35 is tilted together with the cartridge 28. The cartridge is brought into contact with a push rod actuator 74, which presses a defined quantity of material out of the cartridge 28 into the print head.

After dispensing the cartridge 28 may be cleaned in a washing cup 75, which may be lifted by a washing cup actuator 76.

It should be noted here that the description of the invention has been made with reference to exemplary, but not limited to, embodiments. Any alteration or modification in shape, dimensions, morphology, materials and components used in manufacturing and assembling, if they are not a new inventive step and do not contribute to the technical development of the already known one, are considered to be within the scope and purpose of the present invention.

ASPECTS OF THE INVENTION

I. A system for producing tablets, granules and capsules via 3D printing, comprising a display (1), a base (11) with a built-in computer unit (14), a power cable (9), and a 3D printing machine (2) within a chamber (7) with a door (8), with a system of mechanical arm (3) movable in one or more directions, with a base system (4) movable in one or more directions carrying a base (6) and with a print head (5) on the mechanical arm system (3), with a nozzle (37) and a head cylinder (38) with an envelope (39), characterized in that the print head (5) applies on the base (6) a prepared mixture (27) for 3D printing of tablets, granules and capsules.

II. A system for producing tablets, granules and capsules via 3D printing, according to aspect I, characterized in that it has ventilation ducts (12) and an air filter (13) for circulating and purifying the air inside the chamber (7).

III. A system for producing tablets, granules and capsules via 3D printing according to aspect I, characterized in that it has a power supply unit (15) with a voltage stabilizer and an uninterruptible power supply (16).

IV. A system for producing tablets, granules and capsules via 3D printing, according to aspect I, characterized in that it has an air conditioning and air drying (17) system linked via air supply and return ducts (18) with the printing chamber (7).

V. A system for producing tablets, granules and capsules via 3D printing, according to aspect I, characterized in that it has an activated carbon filter (19) for the absorption of carbon dioxide.

VI. A system for producing tablets, granules and capsules via 3D printing, according to aspect I, characterized in that it has a vacuum pump (20) and a negative pressure container (21) for creating vacuum.

VII. A system for producing tablets, granules and capsules via 3D printing, according to aspect I, characterized in that it has a wash tank (22), a wash port (23) connected to a cleaning fluid reservoir (24) and a cleaning fluid filtration system (25) for cleaning the print head (5).

VIII. A system for producing tablets, granules and capsules via 3D printing, according to aspect I, characterized in that the mixture (27) is fed to the print head (5) via the cartridge (28).

IX. A system for producing tablets, granules and capsules via 3D printing, according to aspect I, characterized in that the cartridges (28) are arranged on a carrier (35).

X. A system for producing tablets, granules and capsules via 3D printing, according to aspect I, characterized in that the mixture (27) is fed to the print head (5) via a dispensing tube (30) from the container (29).

XI. A system for producing tablets, granules and capsules via 3D printing, according to aspect I, characterized in that the mixture (27) is in filament form.

XII. A cartridge for use in a system for producing tablets, granules and capsules via 3D printing, according to aspect I, within which a printing mixture (27) is contained and which has an end (31) with a cap (32) and a removable lid (33) on the upper side thereof.

XIII. A print head for use in a system for producing tablets, granules and capsules via 3D printing, according to aspect I, characterized in that it has a heated body (42) with indentations (43) and a cooling fan (44) for controlling the temperature of the mixture (27).

XIV. A print head for use in a system for producing tablets, granules and capsules via 3D printing, according to aspect I, characterized in that it has a photopolymer headlamp (45) on the arm (46).

XV. A print head for use in a system for producing tablets, granules and capsules via 3D printing, according to aspect I, characterized in that it has a liquid nitrogen spray nozzle.

XVI. A print head for use in a system for producing tablets, granules and capsules via 3D printing, according to aspect I, characterized in that it carries a worm screw (47) actuated by a servo motor for stirring the mixture (27).

XVII. A print head for use in a system for producing tablets, granules and capsules via 3D printing, according to aspects I and XV, characterized in that the worm screw (47) has a collapsible head (48) for compressing the mixture (27), with holes (49, 50) intended for entering the solvent and discharging the air, respectively.

XVIII. A print head for use in a system for producing tablets, granules and capsules via 3D printing, according to aspect I, characterized in that it has more than one nozzle (37).

XIX. A print base for use in a 3D printing system according to aspect I, characterized in that it has formatted printing locations (49) for shaping the tablet, granule and capsule.

XX. A print base for use in a 3D printing system according to aspect I, characterized in that it has air ducts (50) for the physical or forced air flow on the base (6).

The invention claimed is:

1. A system for producing pharmaceutical objects via 3D printing, comprising:
a 3D printing machine with a mechanical system movable in one or more directions;
at least one print head with at least one nozzle being movable by the mechanical system, the at least one print head comprising a stirring tool arranged in a print head body, the stirring tool being at least partly collapsible;

a base system carrying a print base for receiving a prepared mixture applied by the at least one print head; and wherein the system comprises at least one carrier for holding a cartridge, and the print head body comprises indentations, fins, or channels for guiding a temperature agent.

2. A system according to claim 1, wherein the system comprises a feed line for establishing a fluid connection between the at least one carrier and the at least one print head.

3. A system according to claim 1, wherein the system comprises a magazine unit with the at least one carrier.

4. A system according to claim 3, wherein the magazine unit comprises an actuator.

5. A system according to claim 1, wherein the system comprises at least one moveable push rod for discharging the cartridge.

6. A system according to claim 1, wherein the system comprises at least one of an opening device for opening the cartridge and a closing device for closing the cartridge.

7. A system according to claim 1, wherein the system comprises a reading unit for identifying an identification mark on the cartridge.

8. A system according to claim 1, wherein the print head body has an opening for receiving a fluid substance from the cartridge.

9. A system according to claim 1, wherein the system comprises an energy emitter, which is linked to the at least one print head.

10. A system according to claim 1, wherein the at least one nozzle comprises a plurality of nozzles.

11. A system according to claim 1, wherein the system comprises a cleaning unit constructed and arranged to clean at least one of the at least one print head and the cartridge.

12. A system according to claim 1, wherein the system comprises a temperature control system for adjusting a temperature of the print base.

13. A system according to claim 12, wherein the base system comprises at least one of air ducts and channels for guiding a tempering agent.

14. A system according to claim 1, wherein the print base comprises formatted printing locations for shaping the pharmaceutical object.

15. A system according to claim 1, wherein the print base comprises a thermal conductor.

16. A system according to claim 1, wherein the print base comprises a coating.

17. A system according to claim 1, wherein the base system comprises an object remover.

18. A system according to claim 1, wherein the base system comprises a base holder for receiving the print base.

19. A system according to claim 1, wherein the system comprises a chamber for establishing a controlled atmosphere having at least one of a vacuum system with a vacuum pump, in air conditioning system, an air filter, ventilation ducts, an air drying system, and an activated carbon filter.

* * * * *